(12) United States Patent
Yavari et al.

(10) Patent No.: US 12,718,935 B2
(45) Date of Patent: Aug. 25, 2026

(54) SYSTEM AND METHOD FOR MANAGING SURGICAL ARTICLES DURING A SURGICAL PROCEDURE

(71) Applicant: Stryker Corporation, Portage, MI (US)

(72) Inventors: Fazel Yavari, Portage, MI (US); Justin Michael Andrews, Schoolcraft, MI (US); Brian James VanDerWoude, Portage, MI (US); Dwight Fowler, Holly Springs, NC (US)

(73) Assignee: Stryker Corporation, Portage, MI (US)

( * ) Notice: Subject to any disclaimer, the term of this patent is extended or adjusted under 35 U.S.C. 154(b) by 31 days.

(21) Appl. No.: 19/041,468

(22) Filed: Jan. 30, 2025

(65) Prior Publication Data

US 2025/0174340 A1 May 29, 2025

Related U.S. Application Data

(63) Continuation of application No. 17/622,302, filed as application No. PCT/US2020/048383 on Aug. 28, 2020, now Pat. No. 12,237,076.

(Continued)

(51) Int. Cl.
*G16H 40/20* (2018.01)
*A61B 50/37* (2016.01)
(Continued)

(52) U.S. Cl.
CPC ......... *G16H 40/20* (2018.01); *G06K 7/10217* (2013.01); *A61B 2050/375* (2016.02); *A61B 2090/0804* (2016.02); *A61B 90/98* (2016.02)

(58) Field of Classification Search
CPC ........ G16H 40/20; G16H 40/60; G16H 20/40; G06K 7/10217; A61B 90/98; A61B 2050/375; A61B 2090/0804
See application file for complete search history.

(56) References Cited

U.S. PATENT DOCUMENTS 3,941,132 A 3/1976 Lenaghan
3,965,907 A 6/1976 Hardy et al.
(Continued)

FOREIGN PATENT DOCUMENTS

CN 103384889 A 11/2013
EP 0948940 A1 10/1999
(Continued)

OTHER PUBLICATIONS

Nordicid, "Applying RSSI Filters for Optimal RFID Performance: Read the Expert Guide", wwww.nordicid.com/resources/blog/applying-rssi-filters-for-optimal-rfid-performance/, Sep. 24, 2018, 5 pages.

(Continued)

*Primary Examiner* — Daryl C Pope
(74) *Attorney, Agent, or Firm* — Howard & Howard Attorneys PLLC

(57) ABSTRACT

System and method of managing one or more surgical articles, wherein the surgical article can include a surgical sponge comprising an identification element, and wherein managing can include counting, locating, or both. The identification element can be a RFID tag. The RFID tag stores unique identification information relative to the surgical sponge. The system and method for detecting RFID tags may include varying the power level of the RFID interrogator to improve the accuracy of scanning the RFID tag or tags. A plurality of the RFID-tagged surgical articles (i.e., surgical sponges) may be packaged or bundled via a strap or within a container.

20 Claims, 6 Drawing Sheets

Related U.S. Application Data

(60) Provisional application No. 62/894,300, filed on Aug. 30, 2019.

(51) Int. Cl.
*A61B 90/00* (2016.01)
*A61B 90/98* (2016.01)
*G06K 7/10* (2006.01)

(56) References Cited

U.S. PATENT DOCUMENTS

| | | | | |
|---|---|---|---|---|
| 4,098,728 | A | 7/1978 | Rosenblatt | |
| 4,114,601 | A | 9/1978 | Abels | |
| 4,244,369 | A | 1/1981 | McAvinn et al. | |
| 4,264,575 | A | 4/1981 | Zimmerman et al. | |
| 4,477,256 | A | 10/1984 | Hirsch | |
| 4,626,251 | A | 12/1986 | Shen | |
| 4,639,253 | A | 1/1987 | Dyer et al. | |
| 4,645,499 | A | 2/1987 | Rupinskas | |
| 4,658,818 | A | 4/1987 | Miller, Jr. et al. | |
| 4,711,996 | A | 12/1987 | Drexler | |
| 4,718,897 | A | 1/1988 | Elves | |
| 4,832,198 | A | 5/1989 | Alikhan | |
| 4,917,694 | A | 4/1990 | Jessup | |
| 5,031,642 | A | 7/1991 | Nosek | |
| 5,041,103 | A | 8/1991 | Rupinskas | |
| 5,045,080 | A | 9/1991 | Dyer et al. | |
| 5,049,219 | A | 9/1991 | Johns et al. | |
| 5,057,095 | A | 10/1991 | Fabian | |
| 5,074,840 | A | 12/1991 | Yoon | |
| 5,112,325 | A | 5/1992 | Zachry | |
| 5,231,273 | A | 7/1993 | Caswell et al. | |
| 5,374,813 | A | 12/1994 | Shipp | |
| 5,443,082 | A | 8/1995 | Mewburn | |
| 5,456,718 | A | 10/1995 | Szymaitis | |
| 5,610,811 | A | 3/1997 | Honda | |
| 5,629,498 | A | 5/1997 | Pollock et al. | |
| 5,637,850 | A | 6/1997 | Honda | |
| 5,650,596 | A | 7/1997 | Morris et al. | |
| 5,678,569 | A | 10/1997 | Chew et al. | |
| 5,805,451 | A | 9/1998 | Speas et al. | |
| 5,923,001 | A | 7/1999 | Morris et al. | |
| 5,931,824 | A | 8/1999 | Stewart et al. | |
| 5,991,728 | A | 11/1999 | DeBusk et al. | |
| 6,150,948 | A | 11/2000 | Watkins | |
| 6,307,473 | B1 | 10/2001 | Zampini et al. | |
| 6,653,937 | B2 | 11/2003 | Nelson et al. | |
| 7,017,800 | B2 | 3/2006 | Ulrich et al. | |
| 7,019,642 | B2 | 3/2006 | Nelson et al. | |
| 7,170,415 | B2 | 1/2007 | Forster | |
| 7,633,394 | B2 | 12/2009 | Forster | |
| 7,703,674 | B2 | 4/2010 | Stewart et al. | |
| 7,791,453 | B2 | 9/2010 | Chen et al. | |
| 8,181,860 | B2 | 5/2012 | Fleck et al. | |
| 8,193,938 | B2 | 6/2012 | Halberthal et al. | |
| 8,519,823 | B2 | 8/2013 | Rinkes | |
| 8,519,848 | B2 | 8/2013 | Stern | |
| 8,593,260 | B2 | 11/2013 | Chen et al. | |
| 9,542,663 | B2 | 1/2017 | Colburn et al. | |
| 10,127,356 | B2 | 11/2018 | Colburn et al. | |
| 11,116,598 | B1 | 9/2021 | Fleck et al. | |
| 2002/0049650 | A1 | 4/2002 | Reff | |
| 2002/0070862 | A1 | 6/2002 | Francis et al. | |
| 2003/0196837 | A1 | 10/2003 | Ballard | |
| 2006/0145855 | A1 | 7/2006 | Diorio et al. | |
| 2006/0176152 | A1 | 8/2006 | Wagner et al. | |
| 2006/0197652 | A1 | 9/2006 | Hild et al. | |
| 2006/0238302 | A1 | 10/2006 | Loving et al. | |
| 2006/0238305 | A1 | 10/2006 | Loving et al. | |
| 2006/0244652 | A1 | 11/2006 | Tethrake et al. | |
| 2006/0290472 | A1 | 12/2006 | Onderko et al. | |
| 2007/0083170 | A1 | 4/2007 | Stewart et al. | |
| 2008/0051746 | A1* | 2/2008 | Shen-Gunther | A61M 16/047 604/362 |
| 2008/0100439 | A1 | 5/2008 | Rinkes | |
| 2008/0290995 | A1 | 11/2008 | Bruns et al. | |
| 2009/0021374 | A1 | 1/2009 | Stagg | |
| 2009/0145957 | A1 | 6/2009 | Zancola | |
| 2009/0160638 | A1 | 6/2009 | Jesme | |
| 2011/0139877 | A1 | 6/2011 | Szakelyhidi et al. | |
| 2012/0173440 | A1 | 7/2012 | Dehlinger et al. | |
| 2013/0088354 | A1 | 4/2013 | Thomas | |
| 2013/0181715 | A1 | 7/2013 | Biber | |
| 2014/0184391 | A1 | 7/2014 | Elizondo, II | |
| 2014/0297371 | A1 | 10/2014 | Colburn et al. | |
| 2015/0216610 | A1 | 8/2015 | Augustine | |
| 2015/0324533 | A1 | 11/2015 | Colburn et al. | |
| 2017/0186160 | A1 | 6/2017 | Satish et al. | |
| 2018/0285704 | A1 | 10/2018 | Stewart et al. | |
| 2018/0344429 | A1 | 12/2018 | Stewart | |
| 2019/0000589 | A1 | 1/2019 | Vanderwoude et al. | |
| 2019/0080797 | A1 | 3/2019 | Colburn et al. | |
| 2019/0298478 | A1* | 10/2019 | Aquino | A61B 17/3421 |
| 2021/0085428 | A1 | 3/2021 | Yavari et al. | |
| 2021/0338373 | A1* | 11/2021 | Blair | A61F 13/44 |
| 2022/0246288 | A1 | 8/2022 | Yavari et al. | |
| 2024/0173077 | A1* | 5/2024 | Ghosh | G16H 50/20 |

FOREIGN PATENT DOCUMENTS

| | | | |
|---|---|---|---|
| JP | 2014211863 | A | 11/2014 |
| WO | 9422580 | A1 | 10/1994 |
| WO | 9830166 | A1 | 7/1998 |
| WO | 2006060324 | A1 | 6/2006 |
| WO | 2008063710 | A2 | 5/2008 |
| WO | 2009082620 | A1 | 7/2009 |
| WO | 2011035277 | A1 | 3/2011 |
| WO | 2011075433 | A1 | 6/2011 |
| WO | 2013055616 | A2 | 4/2013 |
| WO | 2015187857 | A1 | 12/2015 |
| WO | 2016040593 | A1 | 3/2016 |
| WO | 2017112051 | A1 | 6/2017 |
| WO | 2018064288 | A1 | 4/2018 |
| WO | 2019028334 | A2 | 2/2019 |
| WO | 2019048944 | A1 | 3/2019 |

OTHER PUBLICATIONS

Association of Operating Room Nurses, "Recommended Practices for Sponge, Sharps, and Instrument Counts", AORN Journal, vol. 83, No. 2, Feb. 2006, pp. 418-433.
International Search Report for Application No. PCT/US20006/040011 dated May 28, 2008, 1 page.
International Search Report for Application No. PCT/US2020/048383 dated Nov. 16, 2020, 3 pages.
Zebra Technologies Corporation, "RFD8500 Quick Start Guide", MN002225A03, Revision A, Apr. 2020, 2 pages.
Zebra Technologies Corporation, "RFD8500 Series Product Specification Sheet", 2020, 4 pages.
Zebra Technologies Corporation, "RFD8500 User Guide", MN002065A06 Revision A, Jan. 2020, 118 pages.
English language abstract for CN 103384889 A extracted from espacenet.com database on Mar. 26, 2025, 2 pages.
English language abstract for JP 2014-211863 A extracted from espacenet.com database on Jan. 30, 2025, 2 pages.

* cited by examiner 120
124
Sponge Type ID
126
Unique Pack ID
128
Sponge #
130
TID Copy
132
Count-Out Bit
134
Checksum
122
TID (Read-Only)

SYSTEM AND METHOD FOR MANAGING SURGICAL ARTICLES DURING A SURGICAL PROCEDURE

REFERENCE TO RELATED APPLICATION

This application is a continuation application of U.S. application Ser. No. 17/622,302, filed Dec. 23, 2021, which is a national entry of International Application No. PCT/US2020/048383, filed Aug. 28, 2020, which claims priority to and all the benefits of U.S. Provisional Application No. 62/894,300, filed Aug. 30, 2019, the entire contents of each are incorporated herein by reference.

BACKGROUND

The present disclosure generally relates to systems and methods for surgical object detection and identification and, more specifically to tracking and managing RFID tagged sponges.

Before and after a surgical procedure, it is important to track the tools and surgical articles utilized during the procedure to ensure proper sterilization and disposal of the tools or articles. It is also important to have an accurate count of the tools or articles to ensure that none of the tools or articles were inadvertently lost or retained inside a patient. A surgical sponge is an example of a surgical article, which may be comprised of absorbent material for soaking up blood and other bodily fluids in and around an incision site. Health care professionals (HCPs) typically follow strict procedures to account for each and every sponge used during a surgery, in view of the risks associated with a surgical sponge being inadvertently retained inside a patient.

In the past, HCPs have relied upon counting surgical sponges by hand, however, manual counting requires handling of and exposure to soiled sponges and is prone to human error. To reduce the potential for retained surgical sponges associated with inaccurate manual counting methods, surgical sponges have been tagged with radio-opaque markers, barcodes, or wireless transponders, such as RFID or LC respondent transponders. Therefore, there is a need to provide for efficient and accurate counting of the surgical sponges to reduce or eliminate the risks associated with surgical articles being retained inside a patient.

SUMMARY

A method of managing an inventory of surgical articles used during a surgical procedure to ensure proper accounting of surgical articles following the surgical procedure is provided. The surgical articles may be surgical sponges. The surgical articles may be implants, towels, suture needles, clips, staples, or other surgical instruments. The method includes providing an inventory of surgical sponges. The inventory includes a first package containing a first surgical sponge of a first sponge type, wherein the first surgical sponge includes a first RFID tag. The first RFID tag stores a first unique identifier associated with the first surgical sponge, first package content information, and a first power level parameter associated with the first sponge type. The first package content information corresponds to a complete content of the first package.

The method includes operating an RFID reader at a default power level and receiving at the RFID reader the first unique identifier, the first power level parameter stored in the first RFID tag, and the first package content information. The method includes reconfiguring the RFID reader to operate at a first power level, different from the default power level, corresponding to the received first power level parameter; operating the RFID reader at the first power level; and receiving a first response set at the first power level.

The method includes comparing the first response set to the first package content information to determine an error status; and identifying the first package content information as counted-in in a database record for the surgical procedure when no error status determined. The method includes reconfiguring the RFID reader to operate at the default power level.

The method includes positioning the first surgical sponge in a body for a surgical procedure; removing the first surgical sponge from the body; and operating the RFID reader and counting-out the first surgical sponge by reading the first RFID tag with the RFID reader and updating the database record for the surgical procedure. The method includes displaying a status of the inventory of surgical sponges identifying a counted-in and counted-out status based on the database record.

In the method, the first package may further contain a plurality of surgical sponges, each surgical sponge including an associated RFID tag storing a unique identifier associated respectively with each surgical sponge in the first package, the first power level parameter. The first package content information on each RFID tag may include information to identify all other surgical sponges in the first package.

In the method, the inventory of surgical sponges may include a second package containing a second surgical sponge of a second sponge type and a third surgical sponge of the second sponge type. The second sponge type may be different from the first sponge type. The second and third surgical sponges, respectively, include a second and third RFID tags, the second RFID tag storing a second unique identifier associated with the second surgical sponge, the third RFID tag storing a third unique identifier associated with the third surgical sponge, the second and third RFID tags also storing second package content information, and a second power level parameter associated with the second sponge type, wherein the second package content information corresponds to a complete content of the second package.

The method may also include after reconfiguring the RFID reader to operate at the default power level, operating the RFID reader at the default power level, and receiving at the RFID reader one of the second and third unique identifiers, the second power level parameter, where the second power level parameter is different from the first power level parameter, and the second package content information. The method may then include reconfiguring the RFID reader to operate at the second power level; and receiving a second response set. The method them includes identifying the second and third surgical sponges as counted-in in the database record when the second and third unique identifiers are present in the second response set. The method may include comparing the second response set to the second package content information to determine an error status.

The method may also include triggering an alert when an error status is determined. Triggering the alert may include any one of sounding an alarm, displaying a warning, activating a tactile response, and combinations thereof. In the method, the error status is determined when the first result set does not match the first package content information.

The method may also include positioning the RFID reader adjacent to a sterile field in which the surgical procedure is performed; and removing the first surgical sponge from the first package after identifying the first surgical sponge as counted-in.

In the method, the steps of receiving the first response set and receiving the second response set may include, respectively, positioning the first package and the second package at a first distance and a second distance from the RFID reader, wherein the first distance is a first preferred read range for the first package and the second distance is a second preferred read range for the second package, and wherein first power level parameter and the second power level parameter are selected so that the first distance and the second distance are within a same read-in range. The preferred read-in range may be between about 12 inches and about 36 inches.

An alternative method of managing an inventory of surgical sponges used during a surgical procedure to ensure proper removal of surgical sponges following the surgical procedure is also provided. The method includes providing an inventory of surgical sponges. The inventory includes a first package containing a first surgical sponge of a first sponge type, wherein the first surgical sponge includes a first RFID tag. The first RFID tag stores a first unique identifier associated with the first surgical sponge.

The method includes operating an RFID reader to read the RFID tags of the inventory of surgical sponges; and receiving, in response to operating the RFID reader, a response signal comprising the unique identifier stored in the RFID tag. The method includes determining a first received signal strength indicator (RSSI) as a measure of a power level of the response signal from the first RFID tag when read by the RFID reader; and identifying the first surgical sponge as counted-in in a database record for the surgical procedure when the first RSSI meets a first predetermined threshold associated with the first sponge type indicated by the first unique identifier.

The method includes positioning the first surgical sponge in a body for a surgical procedure; removing the first surgical sponge from the body; and reading the first RFID tag with the RFID reader and identifying the first surgical sponge as counted-out in the database. The method includes displaying a status of the inventory of surgical sponges identifying a counted-in and counted-out status based on the database record.

In the method, the inventory of surgical sponges may comprise a second package containing a second surgical sponge of a second sponge type, the second surgical sponge comprising a second RFID tag, the second RFID tag storing a second unique identifier associated with the second surgical sponge. The method may also include determining a second RSSI from the second RFID tag; and identifying the second surgical sponge as counted-in in the database when the second RSSI meets a second predetermined threshold associated with the second sponge type indicated by the second unique identifier.

In the method, the first package may contain a single sponge per package, and the second package may contain a plurality of sponges per package. The first RSSI may be higher than the second RSSI.

The method may include positioning the first package at a first distance from the RFID reader. The first distance may be a first preferred read range for the first package. The method may include positioning the second package at a second distance from the RFID reader. The second distance may be a second preferred read range for the second package. The first predetermined threshold and the second predetermined threshold may be selected so that the first distance and the second distance are within a same read-in range. The read-in range may be between about 12 inches and about 36 inches.

A further alternative method of managing an inventory of surgical sponges used during a surgical procedure to ensure proper removal of surgical sponges following the surgical procedure is provided. The method includes providing an inventory of surgical sponges. The inventory may include a first package containing a first surgical sponge of a first sponge type. The first surgical sponge includes a first RFID tag. The first RFID tag stores a first unique identifier associated with the first surgical sponge, first package content information, and a first assigned power level associated with the first sponge type. The first package content information corresponds to a complete content of the first package.

The method includes operating an RFID reader at a first power level for a first limited period of time to read RFID tags of the inventory of surgical sponges; collecting a first response set during the first limited period of time; and evaluating the first response set to determine a complete first package when the first response set matches the first package content information such that all surgical sponges within the first package are present in the first response set. The method also includes determining whether the first power level matches the first assigned power level; and identifying the first surgical sponge as counted-in in a database record for the surgical procedure when the complete first package is determined and the first power level matches the first assigned power level. The method includes reconfiguring the RFID reader to operate at a second power level for a second limited period of time. The second power level is different from the first power level.

The method includes positioning at least one of the counted-in surgical sponges in a body for a surgical procedure; removing the counted-in surgical sponges from the body; and operating the RFID reader and counting-out the first surgical sponge by reading the first RFID tag with the RFID reader. The method includes displaying a status of the inventory of surgical sponges providing a number of counted-in and counted-out surgical sponges for each type of surgical sponge.

In the method, the inventory of surgical sponges further comprises a second package containing a second surgical sponge and a third surgical sponge, the second and third surgical sponges being of a second sponge type, wherein the second sponge comprises a second RFID tag, the second RFID tag storing a second unique identifier associated with the second surgical sponge, second package content information, and a second assigned power level associated with the second sponge type. The third sponge comprises a third RFID tag. The third RFID tag stores a third unique identifier associated with the third surgical sponge, second package content information, and a second assigned power level associated with the second sponge type. The second package content information corresponds to a complete content of the second package.

The method may also include operating an RFID reader at the power level for a second limited period of time; collecting a second response set during the second limited period of time; evaluating the second response set to determine a complete second package when the second response set matches the second package content information such that all surgical sponges within the second package are present in the second response set and to determine whether the second power level matches the second assigned power level; and identifying the second and the third surgical sponges as counted-in in the database record for the surgical procedure when the complete second package is determined and the second power level matches the second assigned power level.

A system for managing an inventory of surgical sponges used during a surgical procedure to ensure proper removal of surgical sponges following the surgical procedure is also provided. The system includes an inventory of surgical sponges. The inventory includes a first package containing a first surgical sponge of a first sponge type. The first surgical sponge comprises a first RFID tag. The first RFID tag stores a first unique identifier associated with the first surgical sponge, first package content information, and a first power level parameter associated with the first sponge type. The first package content information corresponds to a complete content of the first package. The system also includes an RFID reader configurable to operate at one of a plurality of power levels in response to receiving a power level parameter in response to an RFID read operation.

The system includes a database configured to store data representing a status of the inventory of surgical sponges identifying a counted-in quantity and a counted-out quantity. The RFID reader is configured to operate at a default power level. The RFID reader is configured to receive the first unique identifier, the first power level parameter, and the first package content information. The RFID reader may reconfigure to operate at a first power level, different from the default power level, corresponding to the received first power level parameter; and to operate at the first power level. The RFID reader receives a first response set at the first power level and identifies the first surgical sponge as counted-in in a database record for the surgical procedure when the first unique identifier is present in the first response set; and compares the first response set to the first package content information to determine an error status. The system also includes a display device to display a status of the inventory of surgical sponges identifying a counted-in quantity and a counted-out quantity.

In the system, the inventory of surgical sponges may include a second package containing a second surgical sponge and a third surgical sponge. The second and third surgical sponges are a second sponge type. The second sponge includes a second RFID tag. the second RFID tag stores a second unique identifier associated with the second surgical sponge, the second package content information, and a second assigned power level associated with the second sponge type. The third sponge includes a third RFID tag. The third RFID tag stores a third unique identifier associated with the third surgical sponge, second package content information, and a second assigned power level associated with the second sponge type. The second package content information corresponds to a complete content of the second package.

The RFID reader is further configured to operate at the default power level; receive the second unique identifier, the second power level parameter, and the first package content information. The RFID reader reconfigures to operate at the second power level, different from the first power level, corresponding to the received second power level parameter; and operate at the second power level. The RFID reader receives a second response set at the second power level; and identifies the second and the third surgical sponges as counted-in in the database record for the surgical procedure when the second and the third unique identifiers are present in the second response set; and compares the second response set to the second package content information to determine an error status.

The RFID reader may further trigger an alert when an error status is determined. The alert may include any one of an alarm, a warning, a tactile response, and combinations thereof. The error status is determined when the first result set does not match the first package content information.

An alternative system for managing an inventory of surgical sponges used during a surgical procedure to ensure proper removal of surgical sponges following the surgical procedure is provided. The system includes an inventory of sterile surgical sponges. The inventory includes a first package containing a first surgical sponge of a first sponge type, wherein the first surgical sponge comprises a first RFID tag. The first RFID tag stores a first unique identifier associated with the first surgical sponge, first package content information, and a first power level parameter associated with the first sponge type. The first package content information corresponds to a complete content of the first package. The inventory of surgical sponges includes a second package containing a second surgical sponge and a third surgical sponge. The second and third surgical sponges are a second sponge type. The second sponge includes a second RFID tag. The second RFID tag stores a second unique identifier associated with the second surgical sponge, second package content information, and a second assigned power level associated with the second sponge type. The third sponge includes a third RFID tag. The third RFID tag stores a third unique identifier associated with the third surgical sponge, second package content information, and a second assigned power level associated with the second sponge type.

The system includes an RFID reader configurable to operate at one of a plurality of power levels in response to receiving a power level parameter in response to an RFID read operation. The system also includes a database configured to store data representing a status of the inventory of surgical sponges, identifying a counted-in quantity and a counted-out quantity.

The RFID reader is configured to read RFID tags at multiple power levels. The RFID reader is configured to count-in the first package at a first power level when the RFID reader operates at the first power level associated with the first sponge type and determines the first package is complete. The RFID reader is further configured to count-in the second package at a second power level when the RFID reader operates at the second power level, different from the first power level, the second power level associated with the second sponge type, different from the first sponge type, and determines the second package is complete.

The first power level is associated with the first sponge type so that a preferred read range of the first sponge type is between 12 inches and 36 inches from the RFID reader based on a first packaging configuration of the first sponge type; and the second power level is associated with the second sponge type so that a preferred read range of the second sponge type is also between 12 inches and 36 inches from the RFID reader based on a second packaging configuration of the second sponge type.

BRIEF DESCRIPTION OF THE DRAWINGS

Referring now to the drawings, exemplary illustrations are shown in detail. Although the drawings represent schematic illustrations, the drawings are not necessarily to scale, and certain features may be exaggerated to better illustrate and explain an innovative aspect of an illustrative example. Further, the exemplary illustrations described herein are not intended to be exhaustive or otherwise limiting or restricting to the precise form and configuration shown in the drawings and disclosed in the following detailed description.

Advantages of the present disclosure will be readily appreciated as the same becomes better understood by reference to the following detailed description when considered in connection with the accompanying drawings wherein.

DETAILED DESCRIPTION

The present disclosure relates to systems and methods for managing an inventory of surgical articles during a surgical procedure to ensure the proper removal of the surgical articles from the patient following the surgical procedure and thereby prevent the undesirable retention of the surgical articles within the patient.

Figure 1:
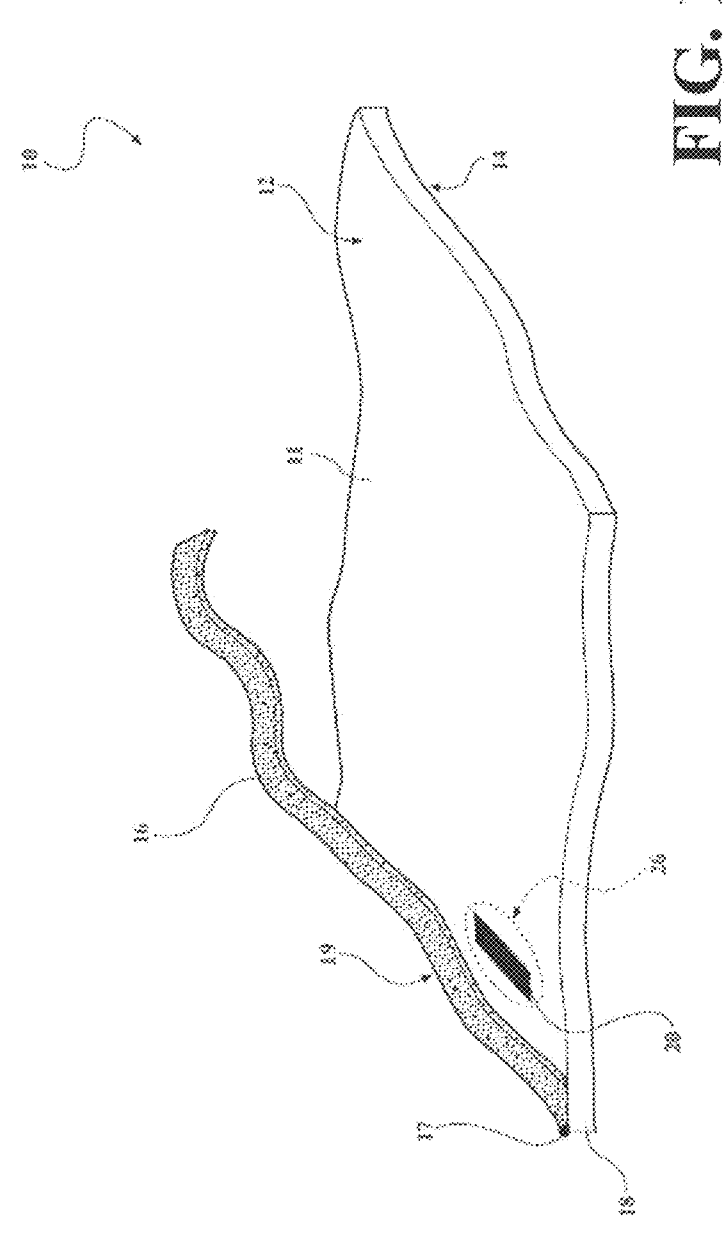
FIG. 1 illustrates a surgical article as a surgical sponge.

FIG. 1 illustrates one such surgical article, a surgical sponge 10, having one or more tags for counting or detecting the surgical article before, during, or after a surgical procedure. In particular, the surgical article illustrated in FIG. 1 may comprise a surgical sponge 10 further comprising a tag 20, as described in detail below. However, while not shown in the Figures, it has been contemplated that other alternatives of the surgical article 10 can include laparotomy pads, gauzes, implants, towels, suture needles, clips, staples, or surgical instruments. Another example of the surgical article may comprise a surgical instrument, such as a scalpel or forceps, comprising a tag 20.

The tag 20 may comprise counting element(s), detecting element(s), or any combination thereof and may be incorporated within handles, between layers of, or other portions of the surgical article 10. As described in detail below, each surgical article 10 can include one or more tags 20, and each tag 20 may include various combinations of the counting elements or the detecting elements. For example, one of these tags 20 may comprise an RFID element (RFID tag). However, each tag 20 can include any number of counting elements and any number of detecting elements, in addition or in the alternative, consistent with the disclosure herein.

The tag 20 may be configured to include unique identification information for each surgical article 10. The unique identification information may comprise a serial number or other identifier that is unique and assigned only to the corresponding article 10. The unique identification information may further convey the type, size, weight, manufacturing dates, expiration date, number of similar articles 10 in a corresponding package, the unique identification of the articles packaged together, or other information used for counting or detecting the article 10.

The tag 20 may convey the unique identification information by transmitting an electromagnetic signal or wave corresponding to the unique identification information. Each surgical article 10 may comprise, in addition, a second tag (not shown) having the unique identifier or other information in a form scannable by an optical-scanning device or human-readable that can be manually entered into a user interface of the scanning device, computer, or other system. A plurality of tags on a surgical article may be different from one another, yet include the same unique identification information related to the specific surgical article to which the tag is affixed. The tag 20 may allow an HCP to identify the number of surgical articles 10 present or to determine a location of the surgical articles 10 within the body of the patient, within an operating room, or both inside the body of the patient and within the operating room. In other alternatives, the tag(s) 20 may be detectable within the operating room but not within the body of the patient.

The tag 20 may be incorporated within handles, between layers of, or other portions of the surgical article 10. For example, the tag 20 can be adhered to or encapsulated within the layers of the surgical article 10, embedded within the handle, or coupled to other portions of the article 10. Each tag 20 may be rigid to increase its service life. In other examples, the tag 20 can be flexible to permit the surgical article 10 and the tag to be folded or otherwise shaped in a more preferable manner for use within a patient's body. Furthermore, the tag 20 may be encapsulated in a biocompatible plastic coating, pouch, or housing 26 that is water-impermeable and sterilizable. The housing 26 may be coupled to the surgical article 10 via stitching, adhesive, or similar type of fastener.

The counting or detecting elements of the tag 20 may be configured to cooperate with at least one detector-interrogating antenna (detecting antenna) of a reader, as a scanning device, such as a hand-held device manipulatable by the HCP. Alternatively, a detector-interrogating antenna may be incorporated into a surgical instrument tray, surgical cart, or canister. However, it is contemplated that any suitable antenna, including one integrated within the optical-scanning device can be configured to detect the detecting element included in the tag 20. The antenna may further comprise a circuit, coil, or loop configured to define a plane of the antenna, wherein a signal, which can be carried on, or understood as, an electromagnetic field, may be transmitted outward from the plane of the antenna, to be received by the tags 20 which then provide a response signal that can be projected back to the antenna. The Applicant has described a scanning device or scanning apparatus with an antenna in U.S. Pat. No. 8,181,860, filed on Sep. 13, 2007, the disclosure of which is hereby incorporated by reference.

A wide variety of tags may be commercially available by a number of manufacturers. Certain tags may be configured to provide significant amounts of user accessible memory, sometimes in the form of read-only memory or write-once memory. One exemplary tag is an RFID tag 20 detectable by a RFID antenna. However, it is contemplated that the surgical article 10 can include any suitable tag detectable by any corresponding detecting antenna. The Applicant has described a surgical article 10 and method of managing surgical articles that comprise various tags in PCT Application No. PCT/US2016/057077, filed on Oct. 14, 2016, the disclosure of which is hereby incorporated by reference.

The surgical article may comprise a surgical sponge 10 comprising an absorbent material body 11. The absorbent material body 11 of the surgical sponge 10 may comprise a top surface 12 and an opposing bottom surface 14. The surgical sponge 10 may further comprise a lead, handle or string 16. The lead 16 may comprise a radio opaque marker material that is configured to show up in a medical scan. For example, the lead may comprise a radio opaque marker material configured to show up in an MRI image to allow for identification of a surgical sponge 10 that was inadvertently retained within a patient.

It may be important for HCPs to track surgical sponges 10 before, during, and after a surgical procedure to ensure that a surgical sponge 10 is not inadvertently retained or left within a patient. Therefore, as described above, an RFID tag 20 may be utilized to identify the location and number of sponges used in a surgical procedure. An RFID tag 20 may be coupled to the top surface of the absorbent material body 11 proximate to an edge or corner of the surgical sponge 10. While not shown in the Figures, it is contemplated that the RFID tag 20 may be incorporated into the handle, between layers of the absorbent material or other portions of the surgical sponge 10 in any number of ways. For example, the RFID tag 20 can be adhered to or embedded within the handle or coupled to other portions of the surgical sponge 10.

The detecting element of the RFID tag 20 may be used with a multiplex detection system. The RFID tag 20 can include a capacitor and an antenna (not shown), which receives power from the detecting antenna (RFID antenna) of the reader to charge the capacitor of the RFID tag 20. This capacitor becomes the power source for the operation of an unpowered RFID tag 20. The RFID tag 20 can have an integrated circuit, which includes a reading function, a carrier frequency modulating function, and a read-only memory portion with a burned-in code. The integrated circuit and corresponding antenna of the detecting element are encapsulated in an enclosure that is resistant to blood, water, or saline solution. Thus, the RFID tag 20 can withstand repeated sterilization and be attached to other surgical articles, such as metal instruments, which are sterilized and reused multiple times. Depending on the carrier frequency and the type of RFID tag 20, the RFID tag 20 can vary significantly in cost, size, and resistance to shielding by intervening tissue.

One feature provided by RFID based technology is that the RFID tag 20 achieves the dual purpose of detecting the location of the surgical sponge 10 in addition to counting or identifying the surgical sponge 10. Thus, certain RFID tags 20 may serve as both detection elements and counting elements. The RFID tag cooperates with the detecting antenna of the reader to both detect the location of the surgical sponge 10 and provide data for determining the unique identification information of the surgical sponge 10. The RFID tags 20 may operate above the MHz range. Exemplary frequencies can include about 13.35 to 14.15 MHz (high frequency), a range from 850 to 950 MHz (ultra-high frequency), or a range of microwave frequencies (i.e., 2.45 to 2.55 GHz). The added bandwidth provided by these RFID tags 20 can increase the probability of detecting and finding the corresponding surgical sponge 10 within the interrogation zone and within a short period of time.

Figure 2:
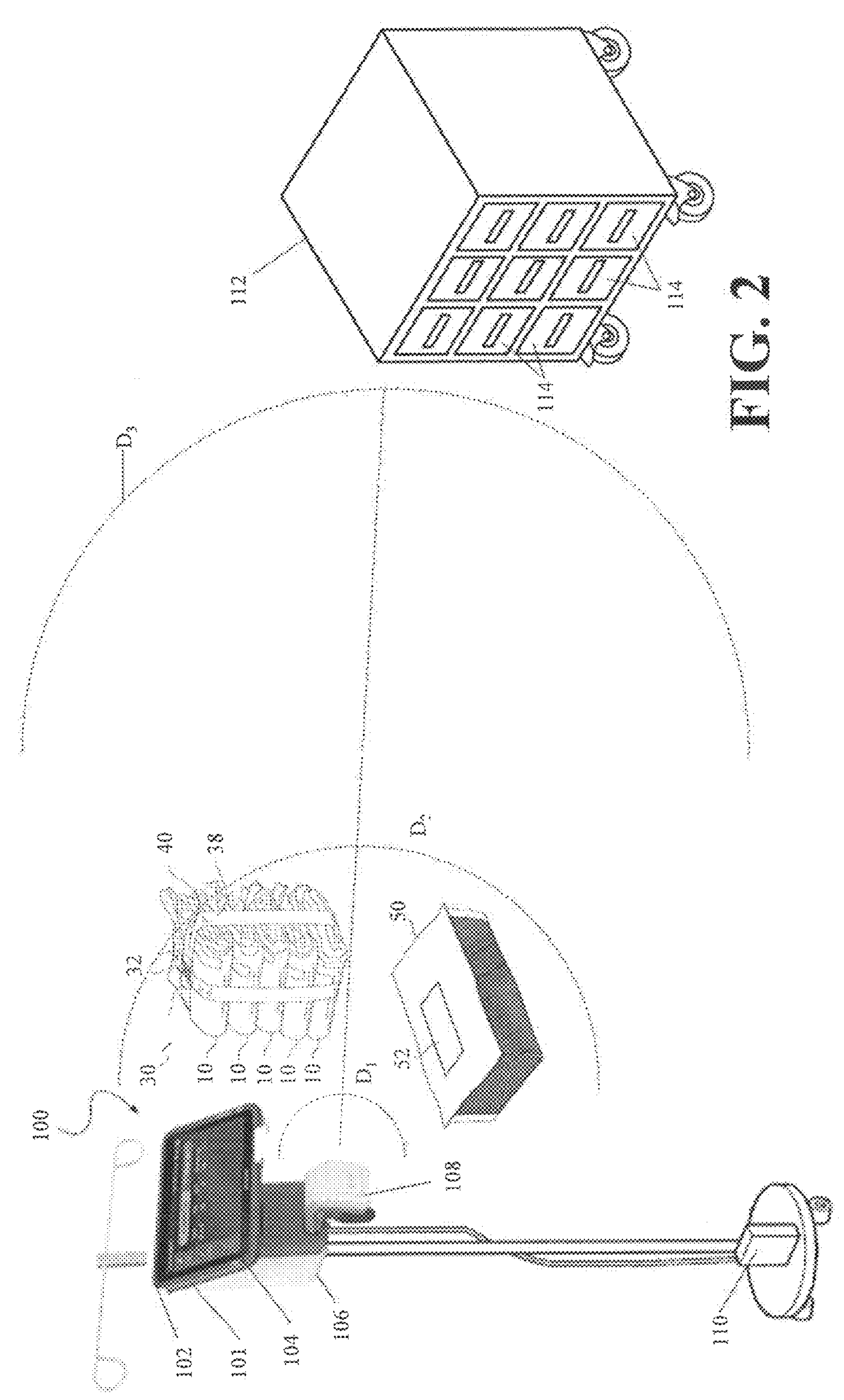
FIG. 2 illustrates an exemplary system to manage an inventory of surgical articles showing a first and second article package within a read range of an RFID reader and an inventory of surgical articles at a distance from the RFID reader.

Turning now to FIG. 2, a system for detecting, identifying and managing an inventory of surgical objects during a surgical operation is disclosed. The scanning device may be configured to maintain a record of the surgical articles 10 used in the procedure in on-board memory, or in cooperation with a server. The scanning device includes an RFID interrogator in communication with the on-board memory. The RFID interrogator includes the physical components and the operating software for generating and receiving the radio frequency signals. Among the physical components of the interrogator are the radio controller, including a signal-generating transmitter, a signal receiver, or a transceiver.

The record of the surgical articles created and maintained by the system may be stored on the scanning device in on-board memory, or else the record may be communicated to a server for storage. The scanning device may have a wired or a wireless connection to the server. In some alternatives, there may be one or more devices disposed in communication between the scanning device and the server. In one example, the scanning device within an operating room may communicate with a computer located in the operating room that is in further communication with other medical devices and tools in the operating room. The computer may communicate information to a router that acts as a gateway to a network. The server is also connected to the network, and thus the scanning device communicates with the server through multiple layers of devices.

At the conclusion of the surgical procedure, the records can be transmitted to a server and matched with patient records, such as electronic medical records, to update the same and provide an indication of which specific surgical articles were used with each patient at which times.

In FIG. 2 examples of various containers for packaging or bundling two or more surgical sponges 10 are shown. A strap 38 or plurality of straps 38 may be utilized to bundle or package two or more surgical sponges 10 together. The strap(s) 38 may be configured to bundle the two or more surgical sponges 10 to maintain a defined relationship between the RFID tags 20 of adjacent surgical sponges 10 in the bundle 30. For example, a plurality of surgical sponges 10 may be stacked on top of one another and packaged together by a strap or band 38. The strap 38 may be configured to bundle 2, 3, 5, 10, 20, or more surgical sponges 10 together. Alternatively, one, or two or more surgical sponges 10 may be packaged or bundled within a pouch or container 50. The container 50 may be similarly configured to the strap, wherein the container 50 is configured to maintain a defined relationship between the RFID tags 20 of adjacent surgical sponges 10 in the container 50. The container 50 may comprise a poly-Tyvek® pouch, a rigid base with a poly-Tyvek® cover, or similar containment apparatus. Any number of surgical sponges 10, or surgical instruments may be packaged or bundled by the strap 38 or within the container 50.

Bundling or packaging surgical sponges 10 as described above can create challenges for scanning the RFID tag(s) 20 of the individual surgical sponges 10 included in the bundle 30. When attempting to scan the RFID tag 20 of the surgical sponges 10 when packaged, one potential challenge is that there is an increased possibility of interference between the RFID tags 20 that may result in an inaccurate count or reduced detection distance of the surgical sponges 10. Providing a sufficient detection distance is important for surgical tools and articles because the sterility of the surgical tools and articles needs to be maintained and the RFID reader may not be sterile or available within the sterile field. If the read distance is insufficient the HCP will need to spend additional time and incur additional costs to sterilely drape the scanner prior to each surgery. On the other hand, simply increasing the scanner power output to overcome the challenges of densely packaged RFID-tagged surgical articles may result in the undesirable counting-in of surgical sponges being transported or stored nearby, including in adjacent operating rooms or other storage locations. Accidental count-in of surgical articles not intended for the active surgical procedure may cause HCPs to waste time and extend the length of a surgical procedure while attempts are made to account for surgical articles never intended to be used in the procedure.

A system 100 for managing surgical articles during a surgical procedure is illustrated in FIG. 2. The system 100 includes the hardware and software to communicate with RFID-tagged surgical articles, create and maintain database records managing an inventory of the surgical articles, including identifying type number, type, and unique identification of those surgical articles made available for use in a particular surgical procedure. The system 100 provides the interface for an HCP to enter information into the database, and to access that information and other information in the database before, during and after a surgical operation.

The system 100 includes a system computer 101 in communication with a display 102. The display 102 may be an integrated display, such as a tablet computer that further includes a touchscreen 104, or other input hardware (not shown). In other alternatives the display 102 may simply be a monitor with the system computer 101 and input functionality provided by other hardware in communication with the display 102. Other input hardware (not shown) may include a microphone for voice command control, or a video camera or other sensor to provide gesture control. Further alternative input hardware may include a trackball, touchpad, keyboard, mouse, or the like.

The display 102 may be supported on a base 106. The base 106 may be pole mounted, as illustrated in FIG. 2. In other alternatives, the base 106 may be a mobile cart, or a stationary unit. The base 106 may be a mechanical support for the display 102 as an integrated display including the power source, computing and input functionality all in the display itself, such as a tablet computer. Alternatively, the base 106 may support functions that are not integrated within the display 102. For example, the base 106 may include the system computer 101, and a rechargeable battery to provide power to the system 100, including providing power to the display 102. The base 106 may house a central processing unit, memory device, data storage device, other hardware for the system computer 101.

The base 106 may also support a RFID reader 108 in communication with the system computer 101. The RFID reader 108 may be integrated into the base 106 or may be removable and operate remotely from the base 106. The base 106 may provide a dock for a removeable, mobile RFID reader, such as a hand-held RFID reader 108. When docked in base 106, the RFID reader may rely on a power source external to itself and may use wired dock connections for communication with the system computer 101.

The RFID reader may include an RFID transceiver enabling communication between the RFID reader 108 and an RFID tag, such as tag 20 of surgical sponge 10. The RFID reader 108 may include its own power source, data processing, and memory or data storage devices internal to the RFID reader 108. The RFID reader 108 may be configurable to operate with varying levels of power provided to the RFID transceiver to change the effective output of radio energy from the antenna.

The system 100 may include or be in communication with an external computing device 110. This may include additional memory or data storage. The device 110 may provide wireless connectivity of other systems, such as a router or modem to communicate with remote resources, such as a hospital network or internet server. In other alternatives, network connectivity is integrated into the system computer 101 without the need for an external device 110.

The system 100 may be provided within a surgical environment such as a hospital operating room. The system 100 may be adapted to be draped for positioning in the sterile field. Alternatively, the system 100 may be positioned adjacent to but outside of the sterile field to avoid the need for sterile draping. In further alternatives, the base 106 may be positioned outside of the sterile field, but the mobile RFID reader 108 may be separate from the base 106 and enter into the sterile field with appropriate sterile draping or other sterilization-maintaining measures as may be known in the art.

The system 100 may be provided with an inventory 112 of surgical articles tagged with RFID tags to be managed during the surgical procedure. In FIG. 2, the inventory of surgical articles is illustrated as a mobile cabinet or cart with drawers 114 containing the supply of a number of different types of RFID tagged surgical articles, such as surgical sponge 10. As described above, surgical sponges 10 may be packaged or bundled in various quantities. RFID-tagged surgical sponges 10 come in a variety of shapes from as small as 2 inches by 2 inches to as large as 8 inches by 108 inches. There are also thickness variations in the number of layers that make up a single surgical sponge 10. For example, some surgical sponges 10 may be as few as 4 ply or as many as 32 ply. Most commonly, surgical sponges 10 are packaged from singly in a package up to 10 units within a package.

Figure 3:
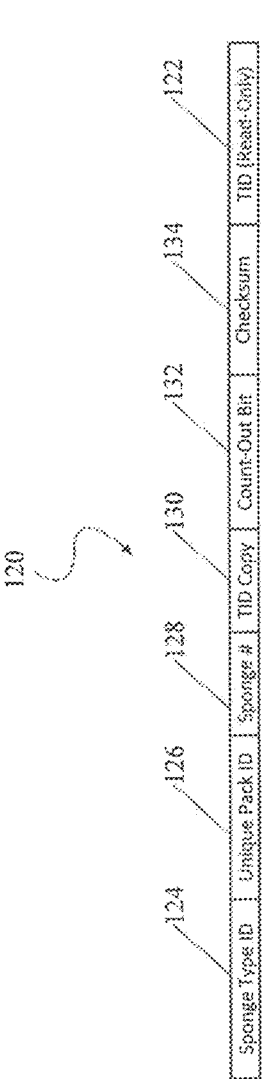
FIG. 3 illustrates an identification scheme of information that may be stored on an RFID tag.
Figure 3:

Each of the surgical articles, e.g., surgical sponges 10, is tagged with an RFID tag, e.g., tag 20, containing data to uniquely identify the individual item as well as provide other information relevant to manage an inventory of surgical articles. Referring now to FIG. 3, an exemplary identification scheme 120 that may be stored in the RFID tag 20 is shown. A variety of tags and data encoding schemes are presently available and the description of the identification scheme 120 is not intended to be limiting. Generally, RFID tags will be manufactured with a tag identification (TID) 122 assigned by the manufacturer of the RFID integrated circuit (IC). This TID 122 is typically stored in a write-once memory location, otherwise known as a read-only memory location on the IC. In addition to the TID 122 provided by the tag manufacturer, other information may be provided in connection with associating the tag IC to a particular surgical article, such as surgical sponge 10.

The identification scheme 120 may include a portion 124 dedicated to identifying the type of surgical article to which the tag is affixed, i.e., sponge type ID. In one alternative, the sponge type ID 124, as described above is a value which may be used by the system computer 101 in combination with a look-up table to retrieve further specification information relevant to the sponge type, such as quantity of sponges for that sponge type, name to be displayed on the user-interface, a designated power level for the RFID reader to operate at while counting-in sponges of that type. The look-up table may be stored local to the system computer 101, such as in data storage of an integrated display 102, data storage provided in the base 106, data storage of an external computer device 110, or remotely from the system computer 101, such as on a hospital network or internet server location. In other alternatives, the sponge type ID 124 may be encoded to provide certain information directly, rather than requiring correlation to a look-up table value. For example, the sponge type ID 124 may correspond directly to a designated RFID reader power level associated with the particular type of sponge. In either case, the sponge type ID 124 may correspond to a power level parameter stored on the RFID tag associated with the sponge type. The power level parameter may directly encode a power level value in dBm, or may otherwise provide data corresponding to a power, current, voltage, or other setting for the reader in controlling or modulating power output, directly or indirectly, from the antenna of the reader. In other alternatives, the sponge type ID 124 may be correlated to or encoded with an RSSI threshold associated to the sponge type and a minimum read strength for counting-in the surgical article to the surgical procedure, as described in greater detail below.

The identification scheme 120 may include information serving to identify the package of sponges, how many sponges are in a package and where a particular sponge falls within that quantity. For example, the identification scheme may include a unique package ID 126 and a sponge number 128. Each package of sponges may be assigned a unique identification that will be shared by all members common to a single package. The unique package ID 126 may also be encoded such that certain values within the unique package ID serve to identify or designate the package as being of a particular type of surgical article. The unique package ID 126 may also be encoded such that certain values identify the quantity of sponges within the package. For each sponge 10 in a package, the sponge number 128 differentiates it from the other sponges in the package. For example, in a package of ten sponges 10, there is one sponge with sponge number 128 of 1, one sponge with 2, and so on up to sponge number 128 of 10. Together, the unique package ID 126 and the sponge number 128 may represent package content information stored on the tag.

The identification scheme 120 may include a copy 130 of the read-only TID in the rewritable memory as a security measure to ensure that the written data has been uniquely assigned and not copied from a previous tag. The TID copy 130, either alone, or in combination with other data stored on the tag may serve as a unique identifier to uniquely identify the sponge to which the tag is affixed. As a further potential security measure, or a way to ensure that the data has not been corrupted, in the identification scheme 120 is the checksum 134. All or a portion of the data contained in the identification scheme on a tag 120 may be used as an input for a mathematical algorithm to generate a checksum value. The particular mathematical algorithm may be proprietary to the sponge manufacturer to ensure that its tags are uniquely identifying only first-party produced sponges, or sponges produced by an otherwise authorized party. A simple example of such an algorithm may be to sum all the values in the other data fields of the identification scheme 120, divide the sum by a given constant, and use the remainder as the checksum value. Without knowing the particular constant used in the algorithm, unauthorized products may be detected by the system computer 101 as a step of the count-in process where the tag data is verified for authenticity.

The identification scheme 120 may include a provision to write to the tag in the course of the count-in or count-out process. For example, identification scheme 120 in FIG. 3 includes the count-out bit 132 which is a flag that is toggled after a sponge has been counted-out. This toggle may be accomplished, for example, by sending instructions from the RFID reader operating in a count-out mode instructing the tag to change the value of this data field upon being counted-out at a conclusion of a surgical procedure. This value may be particularly advantageous in an emergency situation where RFID-tagged sponges are used with a patient without completing the normal count-in procedure. The count-out bit 132 is a value toggled during the process and may be used by the system computer 101 in correctly managing the inventory of surgical articles during a surgical procedure.

The system 100 manages the inventory of surgical articles during a surgical procedure based on the information stored on the RFID tags of the surgical articles, such as surgical sponges 10 and RFID tags 20. The system 100 may include a database of records storing information necessary to manage the inventory of surgical articles, specifically identifying the counted-in and counted-out status of surgical articles associated with particular surgical procedures. In particular, the system 100 may be configured to count-in the surgical articles at the beginning of a surgical procedure by scanning the articles with the RFID reader 108, and to count-out the surgical articles at the end of the procedure. To overcome the challenges of variable package quantities and different types of surgical articles, e.g., different sizes of sponges in one package versus another, that may be used within a surgical procedure, the RFID reader 108 may be configured to operate with a dynamic power level based on a power level parameter stored on the tag or retrieved from a look-up table based on data stored on the tag.

More specifically, the system 100 may operate the RFID reader 108 first at a default power level. This default power level may represent a mid-range value within the full scope of capability of the RFID reader 108. Alternatively, the default power level may be a high extreme or low extreme value depending on the desired first read result set. For example, in an environment with close proximity to storage, such as where the base 106 is mounted to an extension of inventory cabinet 112, it may be desirable to set the default power level to a low extreme value of the RFID reader's 108 capability. In this way, the system 100 will not be overwhelmed with an over expansive result set. In an alternative, it may be desirable to set the default power level to a high extreme value of the RFID reader's 108 capability where the system 100 is disposed at a greater distance from an inventory storage location and from the sterile field where the surgical procedure will occur. Another consideration may be the amount of ambient electromagnetic noise in the environment that may interfere with the consistent communication between the RFID tags 20 and the RFID reader 108.

The system 100 may evaluate the strength of the response signal received from a particular tag and assign an indicator reflective of the strength of the received response. In other words, the system 100 reports the power level of the tag's backscattered response signal in relation to the power level of the RFID reader's initial transmission signal. The response signal strength indicator or RSSI may be used to evaluate the quality of a particular tag's response within the reading zone of the RFID reader.

Operating the RFID reader 108 at the default power level, the system 100 receives in response output signals from the RFID tags 20 within the effective range of the RFID reader 108. In one configuration, included within these signals are the unique identifiers, the power level parameters and the package content information for the surgical articles to which the RFID tags 20 are attached. The system 100 may select a first such response and reconfigure the RFID reader 108 to operate at the power level parameter of the first such response, which is different from the default power level. Once reconfigured, the system 100 operates the RFID reader 108 at the first power level to receive a first response set at the first power level. Within the first response set are the unique identifiers, the package content information and the power level parameters for all the RFID tags 20 responding to the RFID reader's 108 operation at the first power level. Comparing the first response set to the package content information from the first response selected in response to operating the RFID reader at the default power level, the system 100 is able to determine whether a complete first package is present to be checked-in to the surgical procedure or else to determine an error status. This sequence of steps may be repeated until all desired surgical articles have been counted-in for a particular surgical procedure.

In one alternative, for a particular RFID reader power, the system 100 may be configured to count-in only those tagged articles providing a strong enough response signal relative to the RSSI associated with the sponge type. For example, operating the RFID reader at a particular power level may yield a large number of responses representing nearby stored articles. Requiring a minimum RSSI for counting-in a surgical article helps to ensure that only those surgical articles specifically presented to the RFID reader for counting-in will be counted in and actually made available for the surgical procedure, and other nearby articles are not unintentionally included.

It may be important to check the completeness of the package during the check-in process to avoid confusion for the HCP and ensure that the proper and expected quantities and types of sponges are present for the surgical procedure. The system 100, in comparing the first response set to the first package content information, is verifying that all of the expected surgical articles are actually present. For example, in selecting the first response and reconfiguring to the associated first power level parameter, the system 100 is configured to determine an error status if fewer than all the packaged contents are present when interrogated at the power level parameter designated for that sponge type. The power level parameter is specifically arranged for a particular sponge type depending on the packaging configuration—such as, how may sponges are in a packaging, as well as the size and thickness of materials that may interfere with the effective communication of the radio signals. Specifically, the power level parameter for a sponge type is selected in order to maintain a preferred read distance greater than a first distance $D_1$ and less than a second distance $D_2$ between the RFID reader 108 and the package of surgical articles being presented for counting-in. In a first example, the space defined between the first distance $D_1$ and the second distance $D_2$ constitutes the preferred read range the surgical articles at a distance from the reader to maintain their sterile condition, and otherwise to minimize the impact of any quantity of sponges stored in proximity to the system 100, accounting for differences in packaging or manipulation by the HCP. In one example, the first preferred distance $D_1$ is about 12 inches and the second preferred distance $D_2$ is 36 inches measured from the RFID reader.

It should be appreciated that the read range of the RFID reader 108 begins at a zero distance away from the RFID reader 108. A RFID tag placed immediately adjacent to the RFID reader 108 would be responsive to an interrogation at that distance and thus could be read by the RFID reader 108. Differences in packaging density, i.e., how many articles are in a package, potential interference by the article materials, and how the article or package is held by the HCP, are all factors that may affect the response signal quality and thus read reliability. However, placing the surgical articles immediately adjacent to the RFID reader may compromise the sterility of the surgical article. Thus, it is preferable to establish a preferred read range far enough away from the RFID reader to maintain product sterility, but not so far away as to induce responses from surgical articles that are merely stored nearby.

These measurements are merely illustrative and are not intended to be limiting. In other examples, other distances are contemplated for the first and second distances to maintain sterility of the surgical articles and minimize the impact other environmental conditions. For example, the inventory of stored sponges is located at a greater distance $D_3$ than the max preferred read-in distance $D_2$, and thus is intended to be outside the effective read range of the RFID reader 108 during the count-in process.

An exemplary table of sponge types (given, for example, in square dimensions and ply where applicable), the number of that type of sponge within a single package, and an associated power level parameter, corresponding to the effective power output at the antenna of the RFID reader 108, is presented below.

| Package type | Quantity in package | Power, dBm |
|---|---|---|
| 18 × 18 | 5 | 14 |
| 8 × 36 | 5 | 14 |
| 12 × 12 | 5 | 14 |
| 4 × 18 | 5 | 14 |
| 17 × 26 Towels | 5 | 14 |
| 4 × 4-16ply | 10 | 16 |
| 4 × 4-32ply | 10 | 16 |
| 2 × 2 | 10 | 25 |
| 8 × 36 | 1 | 10 |
| 4 × 18 | 1 | 10 |
| 8 × 108 | 1 | 10 |
| 2 × 36 | 1 | 11 |
| 2 × 72 | 1 | 11 |
| 8 × 4-12ply | 10 | 18 |
| 8 × 4-16ply | 10 | 18 |
| 8 × 4-24ply | 10 | 18 |
| 18 × 36 | 3 | 14 |

As detailed in the table, the range of power levels associated with the different packages ranges from 10 dBm to 25 dBm. The power unit dBm (otherwise expressed as $dB_{mW}$) is a unit of level used to indicate a power ratio expressed in decibels (dB) with reference to one milliwatt (mW). The range of package quantities may be between 1 sponge and 10 sponges within a single package, although other quantities are contemplated within the scope of this disclosure. Assuming all else is constant, the more sponges in a package, the higher the associated power level parameter is for the associated sponge type. Packages with only 1 sponge have lower power level parameters. The size of the sponges in a package may affect the power level for the package in addition to considering the number of sponges in the package. For example, several packages are presented in the table above with a quantity of 1 per package, but those sponges with more material—that is, a larger size—are typically associated with a lower power level. In this way, the system 100 effectively manages the inventory of surgical articles during a surgical procedure, avoiding the inadvertent counting-in of nearby stored surgical articles.

It should also be noted that the table above provides illustrative examples of package types by the primary dimensions of the sponges in the package and the quantity of that type of sponge in a single package. This table is not intended to be limiting, and other sizes, quantities, or types of surgical articles are likewise contemplated by the present disclosure.

The power level associated with a particular package type may be determined empirically. For example, to determine a power level for a particular package type and quantity, an example package of that type and quantity may be scanned at a variety of power levels, in a variety of environmental conditions (i.e. in the presence of differing quantities and locations of articles stored in a relative proximity to the scanner), using a factorial design of experiments. The result sets across the different conditions may be evaluated and the result set that provides the highest confidence of reading all articles in the package while minimizing the impact of environmental noise on the successful read of the package contents. It is further contemplated that other methods of determining the preferred power level may also be employed.

In connection with managing the inventory of surgical articles, the system 100 includes the display 102 to communicate the status of the inventory of surgical articles to the HCP. Specifically, the system 100 may display information identifying the types of surgical articles that have been counted-in and the quantity thereof, as well as the quantity of surgical articles that have been counted-out once the article has been removed from the surgical procedure.

The system 100 may also be configured to alert the HCP on the determination of an error status, such as where fewer than all of the quantity of sponges within a package appear in a result set when the RFID reader is configured to operate at a power level parameter corresponding to that article type. The system 100 may display information about the error on the display 102, such as identifying the type of sponge presented, the number counted as present, the number expected within the package, and the discrepancy between the two. The system 100 may, in the alternative or in addition, accompany this alert display with audible alarms, visual alerts such as flashing lights. The system 100 may also activate a tactile response, for example, within the mobile RFID reader 108 if the reader 108 is undocked from the base 106. The tactile response may include a vibration pulse or pattern of pulses.

In an alternative, the bundle 30 may comprise a master tag 32 that may include unique identification information. For example, the master tag 32 may include the number of surgical sponges 10 included in the bundle 30, as well as include the unique identification information for each of the sponges 10 contained in the bundle 30. The master tag 32 may include a unique identification of the package in addition to the unique identifications of the sponges within the bundle 30.

The master tag 32 may be configured to identify the side of bundle 30 or package/object that should be scanned based on the position of the RFID tags 20. For example, the master tag 32 or the packaging 38 may include an indicator 40 to facilitate such placement/orientation, such as an arrow pointing to the side of the bundle 30 that should be scanned for optimal accuracy. Alternatively, an indicator 40 could be placed on the side of the bundle that should be placed closest to the scanner. The indicator 40 may be placed on one or multiple sides of the bundle of sponges 30. The indicator 40 may be placed on any side/face of the bundle.

A container 50 configured to hold an individual sponge, a plurality of sponges, a bundle 30 or plurality of bundles 30 and may comprise a similar master tag 52 configured to identify the contents of the container 50. For example, the container master tag 52 may identify the contents of the container 50, such as the number of sponges, or number of bundles 30 included in the container 50, as well as any additional equipment or medical instruments included in the container 50. A container 50 configured to hold a bundle of surgical sponges 30 may comprise a similar indicator configured to identify optimal scanning orientation/position/movement as described above with regard to indicator 40. A master tag 32, 52 may be provided associated with a bundle 30 or container 50 and may provide human readable, or machine-readable information, for example, an RFID tag, bar code, QR code or the like. The master tag 32, 52 may provide additional information or identical information as provided on the article tags, such as RFID tag 20. The master tag 32, 52 may be useful in performing additional verifications prior to using the articles in a surgical operation.

A first method 400 of managing an inventory of surgical articles used during a surgical procedure is illustrated. The surgical articles may be surgical sponges 10, as described above. Implementing the described method 400 assists HCPs in ensuring the proper removal of surgical articles following the surgical procedure. The method includes a first step 402 of providing an inventory of surgical articles, such as surgical sponges. The inventory may be stored in a container, such as the mobile cabinet 112 shown in FIG. 2. The inventory includes the packages of surgical articles. In a first example, the inventory includes at least a first package containing at least a first surgical sponge of a first sponge type. The first surgical sponge includes a first RFID tag storing a first unique identifier associated with the sponge, first package content information, and a first power level parameter associated with the first sponge type. The first package content information corresponds to a complete content of the first package. The use of designations of "first," or "second" refer only to separate iterations of the count-in method steps and are not intended to be limiting or to require that "first" is different from "second" except where specifically denoted.

As described above, the package may include more than a single article, such as quantities of 2, 3, 5, 10, 20 or more within a single package. The unique identifier may be a single memory data field of an identification scheme stored on the RFID tag or may combine entries of multiple data fields to constitute a single unique identifier. The package content information includes such information necessary to identify the unique package and the content of the package, such as quantity. In one example, the package content information relates to the unique package ID 126 of the identification scheme 120, and may include sponge type ID 124, to retrieve the complete package quantity, and the sponge number 128 identifying which position in the package a particular sponge occupies among the complete quantity.

The method includes a second step 404 of operating an RFID reader at a default power level. The step of operating the RFID reader refers to activating the emission of radio energy to elicit a response for the RFID tags within a range of the RFID reader. To initiate this step, an HCP may provide an input to the RFID reader either directly or through some other connected piece of hardware. The default power level denotes a power level setting of the reader which is not necessarily associated with a particular sponge type. For example, the default power level may represent a midrange of the capability of the RFID reader. Alternatively, the default power level may represent a midrange of the power level parameters associated with the different sponge types which the RFID reader is adapted to read. In one example, a default power level parameter may be 15 dBm. In other alternatives, the default power level may be selected to be one of a maximum or minimum extreme of a capable range of the RFID reader depending on the particular environment in which the RFID reader will be operated, or other considerations as described above.

The method includes the step 406 of receiving, at the RFID reader, a response or responses to operating the RFID reader at the default power level. This step may include the HCP specifically presenting a package of RFID-tagged surgical articles to the RFID reader, or vice versa, positioning them so that the RFID reader is within an effective read range of the RFID reader. The preferred read range may be between 12 inches and 36 inches. The response to step 404 may include one or more tag data. For example, in an environment where multiple RFID tags are present, the RFID reader may employ anti-collision features or read, collect, and process multiple tag's data in one read operation. For example, such anti-collision features are described in the industry standard ISO/IEC 15693-3:2009—Anticollision and Transmission Protocol. The RFID reader is in communication with or incorporates a computer processing device to execute the operations of the method. Information may be retained in a database stored on a memory of the RFID reader, of another computer processing device, or may be distributed among multiple computer processing devices. The description of any processing or computing step may be performed by the RFID reader, or another device which is in communication with the RFID reader.

Among the response data received, a first tag's data is used for continuing the steps of the method 400, the first tag's data including a first unique identifier, the first power level parameter stored in the first RFID tag, and the first package content information for the first tag. The data upon which to continue the method 400 from this step 406, may be the first complete data received in the response time. Alternatively, the response of step 406 may prioritize the use of some types of sponges over other types of sponges or may use other criteria to designate or select a particular sponge to proceed with the steps of the method 400 in order. In one example, the response data received at the default power level may be evaluated to determine whether multiple sponges from a single package are present in the response set. If a minimum percentage of sponges from a single package are present in the response data, the first tag for continuing the steps of the method 400 may be selected from the package having at least the minimum percentage present in the response set. The minimum percentage may be between about 25% to about 50% of the sponges in a complete package. The minimum percentage may be at least 30% of the sponges in a complete package.

Based on the first RFID tag data, the method 400 includes the step 408 of reconfiguring the RFID reader to operate according to the first power level parameter, which corresponds to the first sponge type; and the step 410 of operating the RFID reader at the first power level. This operation constitutes a second interrogation by the RFID reader, but at a different power level from the default power level. The first power level may be higher or lower than the default power level, and this may return more or fewer responsive tags. Where the first power level is higher than the default power level, such as with a sponge type more densely packed with multiple sponges in a single package, more responsive tags may be found as the higher-powered interrogation overcomes the interference caused by the close proximity of the multiple tags. Where the first power level is lower than the default power level, such as with a sponge type packaged singly to a package, fewer responsive tags may be found as the effective read range will be diminished to a closer range. Thus, the method 400 includes step 412 of receiving a first response set at the first power level.

During the step 412 of receiving the first response set at the first power level, the system may be configured to selectively look for a single sponge type, corresponding to the first sponge type. Any response to the interrogation at the first power level that does not match the first sponge type may be automatically excluded from the first response set to reduce the volume of data to be processed.

The method 400 then includes the step 414 of comparing the first response set, in response to operating the RFID reader at the first power level and different from the default power level, to the first package content information to determine an error status. Within the first response set are the unique identifications of all the tags present within the effective read range of the RFID reader at the first power level. Based on the response to step 404 of operating the RFID reader at the default level and receiving the first package content information, a comparison can be made to the first response set—the response from operating the RFID reader at the first power level.

In a situation where the package is complete—that is, no error is present—the first response set will properly contain the identification of all the sponges indicated by the first package content information. Where the first package content information is that of multiple sponges in a single package, this is an important verification that all of the expected articles are actually present so as to minimize errors or confusion for the HCP in managing the use of surgical articles during the surgical procedure and avoiding the undesirable retention of surgical articles within the patient following the surgical procedure. In this case, the complete package of surgical articles may be counted-in to the surgical procedure at step 416 and the articles may be placed in the appropriate staging area to be at hand for the HCP in the surgical procedure. The above steps, beginning with step 404 operating the RFID reader at the default power, may be repeated along branch 417 until the desired inventory of surgical articles has been counted-in and made available for the surgical procedure. As the RFID executes the steps described, different types of sponges may be encountered, having different package quantities and different associated power levels. The different power levels associated with the different package types maintains a preferred read range of between about 12 inches to about 36 inches between the RFID reader and the package of surgical sponge, regardless of sponge type.

Comparing the first response set with the first package content information may indicate that the package is not a complete package. Upon this determination at step 418, the HCP may be alerted to the error. This step may be performed in a variety of ways. For example, a visual alert may be displayed to the HCP on a display in communication with the RFID reader. The visual alert may display specific information about the error, such as identifying the type of sponge presented, the number and identity of responding tags, the number expected within the package, and the discrepancy between the two. In the alternative, or in addition, the HCP may be alerted to an error determination with other visual alerts such as illuminated or flashing lights on a display or on the RFID reader. The HCP may be alerted to an error with an audible alarm, or a tactile response, for example within the RFID reader. The tactile response may include a vibration pulse or pattern of pulses.

Upon being alerted to the error condition, the HCP may remedy the error, if possible, or may discard the incomplete package of sponges and move on to other packages provided in the inventory, proceeding along branch 419, and repeating the steps of method 400 beginning with operating the RFID scanner at a default power level and continuing until the desired inventory of surgical articles have been counted-in and made available for the surgical procedure.

Once the desired inventory of surgical articles has been counted-in, the HCP may proceed with the surgical procedure as step 420. Upon completion of the surgical procedure, the surgical articles are removed from the patient at step 422. Following removal from the patient, the surgical articles are counted-out, for example, by again reading the surgical articles with the RFID reader at step 424. In the alternative, counting-out the surgical article may include optically scanning a label provided on the surgical article, or manually entering information so as to designate the surgical article as counted-out.

During the count-out step 424, the RFID reader may operate at a default power level. Alternatively, the RFID reader may operate at a power level corresponding to a power level parameter of a sponge type counted-in to the procedure and not yet counted-out. Where multiple sponge types are counted-in, with the sponge types having different associated power level parameters, the RFID reader may operate by performing sequential interrogation operations while cycling operations at different power levels associated with the different sponge types. The RFID reader may receive response sets and register only those responses from sponges of the type corresponding to the power level of the particular interrogation cycle, while excluding any response of other types of sponges not associated with the power level of the particular interrogation cycle.

Figure 4:
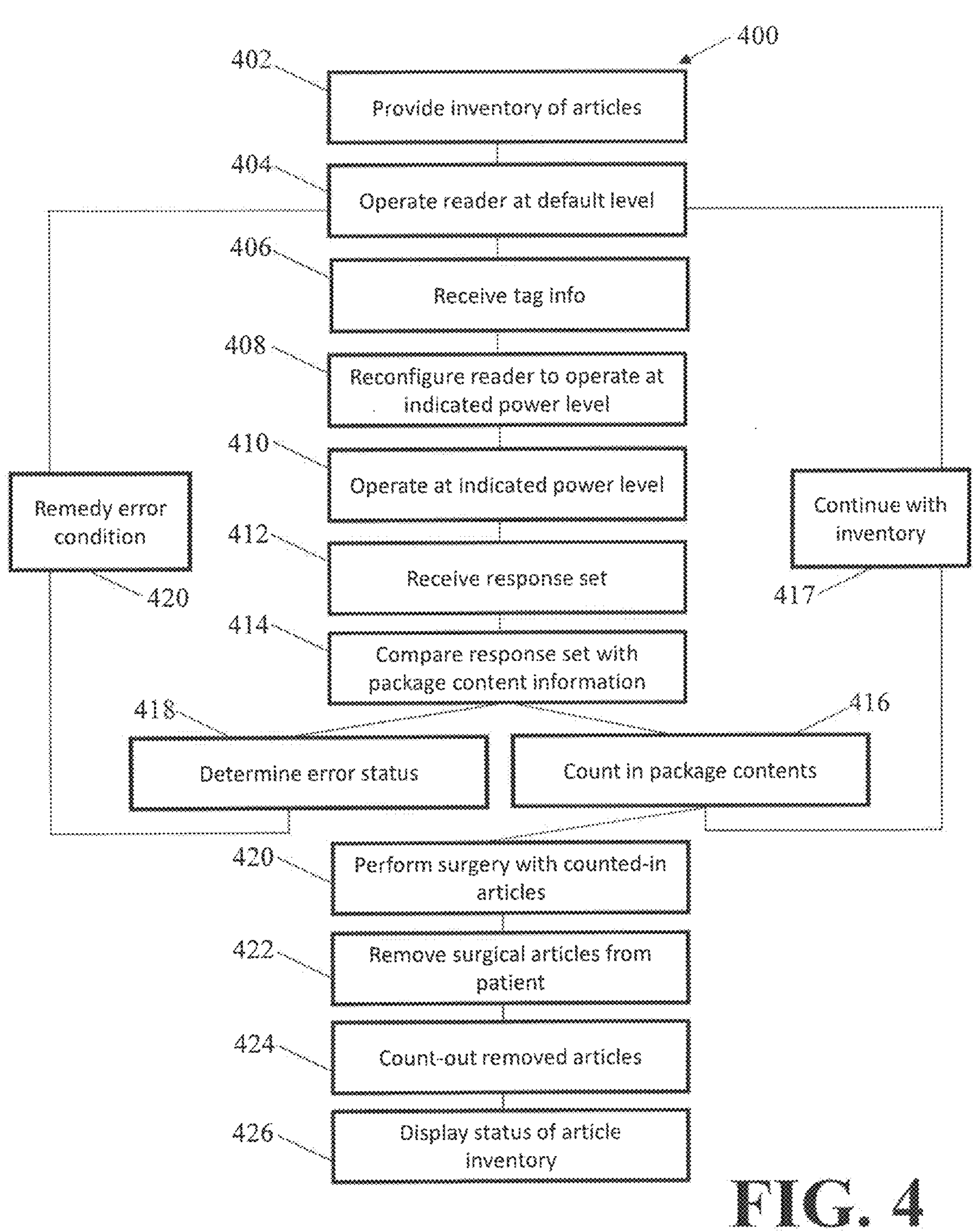
FIG. 4 illustrates a first method for managing surgical articles during a surgical procedure.

The method 400 also includes the step 426 of displaying the status of the surgical article inventory. Although illustrated at the conclusion of the method shown in FIG. 4, it is contemplated that this step may be performed persistently throughout the method, indicating the types of sponges responding to the RFID reader interrogation steps 406, 412, and maintaining a current count of counted-in and counted-out surgical articles as the surgical procedure proceeds. For example, displaying the status of the article inventory may include displaying a specific count of counted-in and counted-out surgical articles for each type of surgical article present. This display of the inventory status provides direct and immediate accounting of the surgical articles present for the surgical procedure to minimize the burden on HCPs in tracking and counting the use of surgical articles and ensuring that no surgical articles are retained in the patient following the surgical procedure.

Figure 5:
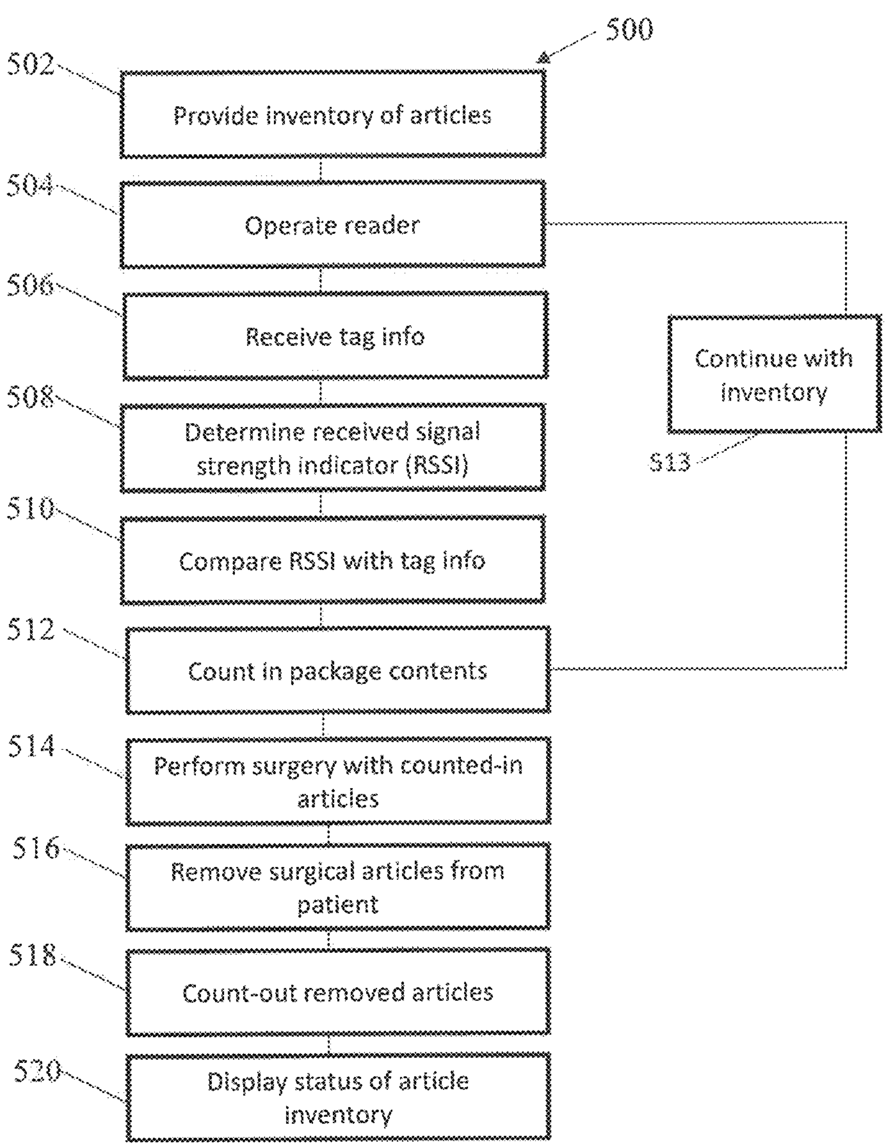
FIG. 5 illustrates a second method for managing surgical articles during a surgical procedure.

A second method 500 of managing an inventory of surgical articles used during a surgical procedure is illustrated in FIG. 5. The surgical articles may be surgical sponges 10, as described above. Implementing the described method 500 assists HCPs in ensuring the proper removal of surgical articles following the surgical procedure. It should be appreciated that any feature/step of any method and system described herein may be used with the other methods and systems described throughout.

The method 500 includes a first step 502 of providing an inventory of surgical articles, such as surgical sponges. The inventory may be stored in a container, such as the mobile cabinet 112 shown in FIG. 2. The inventory includes the packages of surgical articles. In a first example, the inventory includes at least a first package containing at least a first surgical sponge of a first sponge type. The first surgical sponge includes a first RFID tag storing a first unique identifier associated with the sponge, first package content information, and a first power level parameter associated with the first sponge type. The first package content information corresponds to the complete content of the first package. The use of designations of "first," or "second" refer only to separate iterations of the count-in method steps and are not intended to be limiting or to require that "first" is different from "second" except where specifically denoted.

As described above, the package may include more than a single article, such as quantities of 2, 3, 5, 10, 20 or more within a single package. The unique identifier may be a single memory data field of an identification scheme stored on the RFID tag or may combine entries of multiple data fields to constitute a single unique identifier. The package content information includes such information necessary to identify the unique package and the content of the package, such as quantity. In one example, the package content information relates to the unique package ID 126 of the identification scheme 120, and may include sponge type ID 124, to retrieve the complete package quantity, and the sponge number 128 identifying which position in the package a particular sponge occupies among the complete quantity.

The method 500 includes steps 504 of operating an RFID reader and 506 of receiving tag information in response to operating the RFID reader. To initiate this step, an HCP may provide an input to the RFID reader either directly or through some other connected piece of hardware. This step may include the HCP specifically presenting a package of RFID-tagged surgical articles to the RFID reader, or vice versa, positioning them so that the RFID reader is within an effective read range of the RFID reader. The preferred read range may be between 12 inches and 36 inches. The response to step 504 may include one or more tag data. For example, in an environment where multiple RFID tags are present, the RFID reader may employ anti-collision features or read, collect, and process multiple tag's data in one read operation. For example, such anti-collision features are described in the industry standard ISO/IEC 15693-3:2009—Anticollision and Transmission Protocol. The RFID reader is in communication with or incorporates a computer processing device to execute the operations of the method. Information may be retained in a database stored on a memory of the RFID reader, of another computer processing device, or may be distributed among multiple computer processing devices. The description of any processing or computing step may be performed by the RFID reader, or another device which is in communication with the RFID reader.

Among the response data received, a first tag's data is used for continuing the steps of the method 500, the first tag's data includes a first unique identifier and information sufficient to identify a sponge type. The information identifying the sponge type may include or may be used to retrieve an associated RSSI count-in threshold for the particular sponge type. The data upon which to continue the method 500 from this step 506 may be the first complete data received in the response time. Alternatively, the response of step 506 may prioritize the use of some types of sponges over other types of sponges or may use other criteria to designate or select a particular sponge to proceed with the steps of the method 500 in order.

Based on the first RFID tag data, the method 500 includes the steps 508 of determining the RSSI for the first RFID tag response, and 510 of comparing the determined RSSI with the tag information, including the RSSI threshold associated with the sponge type. The RFID reader may determine the RSSI for the first RFID tag response or it may communicate the information related to the first RFID tag response to another computing device, such as a system computer, for processing the first RFID tag response and determining the RSSI. The RSSI is determined as a measure of the power of the response signal relative to the power of the interrogation signal prompting the response.

If the determined RSSI for a particular tag is at or above the RSSI threshold associated with the sponge type, the associated sponge is counted-in to the surgical procedure for use therewith at step 512. It is contemplated that tag responses which do not meet or exceed the associated RSSI threshold for the associated surgical article type do not signify an error about which the HCP must be alerted. Rather, a low RSSI may simply signify a tag response as environmental noise for example, from surgical articles stored nearby, but not intended for use in the surgical procedure. The steps of operating the reader 504, receiving tag information 506, determining 508 and comparing 510 the RSSI values may be continued and repeated until the desired inventory of surgical articles have been checked into the surgical procedure, as shown along branch 513.

The method 500 includes the step 520 of displaying the status of the article inventory. Although illustrated at the conclusion of the method shown in FIG. 5, it is contemplated that this step may be performed persistently throughout the method, indicating the types of sponges responding to the RFID reader interrogation steps 506, and maintaining a current count of counted-in and counted-out surgical articles as the surgical procedure proceeds. For example, displaying the status of the article inventory may include displaying a specific count of counted-in and counted-out surgical articles for each type of surgical article present. This display of the inventory status provides direct and immediate accounting of the surgical articles present for the surgical procedure to minimize the burden on HCPs in tracking and counting the use of surgical articles and ensuring that no surgical articles are retained in the patient following the surgical procedure.

If a particular package of surgical articles is presented by an HCP for counting-in but is not acknowledged by the system, such as by updating the displaying step to add the package quantity and type as counted-in, the HCP may attempt to adjust the positioning of the package relative to the RFID reader by moving it closer to the RFID reader or centering the package in front of the reader. The HCP may attempt to count-in the package by rotating the package to adjust its orientation relative to the RFID reader, or combinations of moving and rotating the package relative to the RFID reader. In some instances, the determined RSSI of a particular article may never achieve the threshold RSSI associated with the article type. The HCP may discard the article as defective in this case. Failure to achieve a sufficiently strong responsive signal at a count-in phase may indicate that the article will fail to provide a responsive signal during a count-out phase, potentially leading to confusion in the HCP attempting to manage and account for the article inventory at the conclusion of the surgical procedure.

Once the desired inventory of surgical articles has been counted-in, the HCP may proceed with the surgical procedure as step 514. Upon completion of the surgical procedure, the surgical articles are removed from the patient at step 516. Following removal from the patient, the surgical articles are counted-out, for example, by again reading the surgical articles with the RFID reader at step 518. In the alternative, counting-out the surgical article may include optically scanning a label provided on the surgical article, or manually entering information so as to designate the surgical article as counted-out.

During the count-out step 518, the RFID reader may operate at a default power level and count-out sponges when a response to the interrogation signal is received and the sponges has been previously counted-in to the procedure. Alternatively, the RFID reader may operate by varying the power level for successive interrogation cycles according to the power level parameters associated with the sponge types counted-in to the procedure. In a further alternative, the RFID reader may combine the technique of variable power levels described above in step 424, with an evaluation of the RSSI for a particular sponge to ensure that the proper sponge is being counted-out. In order to achieve the requisite RSSI during the count-out process, the sponge may be presented within a range of the RFID reader so that sponges remaining in the surgical field are not inadvertently counted-out.

Consistent with the above description, the method 500 includes displaying the status of the article inventory 520, including, for example, providing an identification of counted-in and counted-out articles throughout the surgical procedure.

Figure 6:
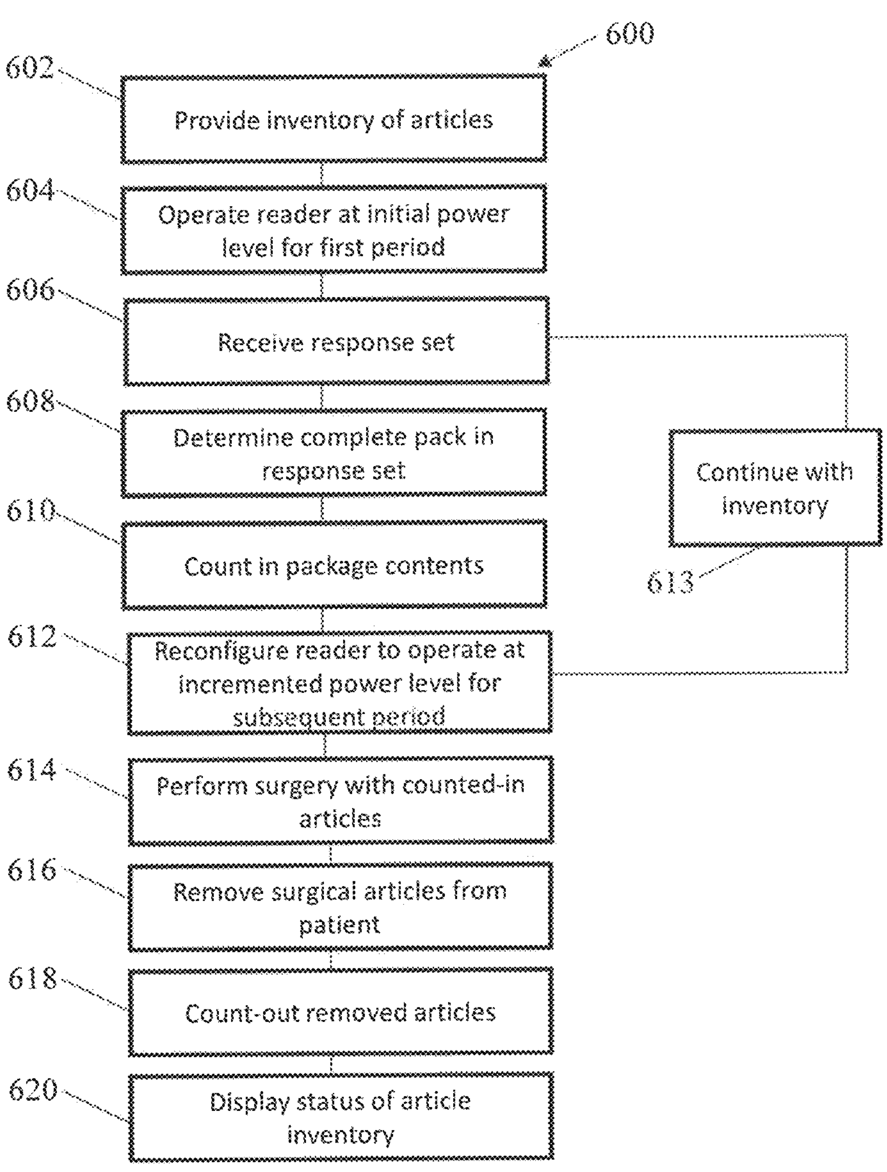
FIG. 6 illustrates a third method for managing surgical articles during a surgical procedure.

A further method 600 of managing an inventory of surgical sponges used during a surgical procedure is illustrated in FIG. 6. Similar to the above methods 400, 500, the surgical articles may be surgical sponges 10, as described above and the method may serve to assist HCPs in ensuring the proper removal of surgical sponges following the surgical procedure. Again, as in the above methods 400, 500, the method 600 includes a first step 602 of providing an inventory of surgical articles, such as surgical sponges. The inventory may be stored in a container, such as the mobile cabinet 112 shown in FIG. 2. The inventory includes the packages of surgical articles. In a first example, the inventory includes at least a first package containing at least a first surgical sponge of a first sponge type. The first surgical sponge includes a first RFID tag storing a first unique identifier associated with the sponge, first package content information, and a first power level parameter associated with the first sponge type. The first package content information corresponds to a complete content of the first package. The use of designations of "first," or "second" refer only to separate iterations of the count-in method steps and are not intended to be limiting or to require that "first" is different from "second" except where specifically denoted.

As described above, the package may include more than a single article, such as quantities of 2, 3, 5, 10, 20 or more within a single package. The unique identifier may be a single memory data field of an identification scheme stored on the RFID tag or may combine entries of multiple data fields to constitute a single unique identifier. The package content information includes such information necessary to identify the unique package and the content of the package, such as quantity. In one example, the package content information relates to the unique package ID 126 of the identification scheme 120, and may include sponge type ID 124, to retrieve the complete package quantity, and the sponge number 128 identifying which position in the package a particular sponge occupies among the complete quantity.

The method 600 includes steps 604 of operating an RFID reader and 606 of receiving tag information in response to operating the RFID reader 604. The step 604 of operating the RFID reader includes operating the RFID reader at an initial power level for a first period of time. During this step 604, the RFID reader collects a first response set during the first limited period of time. Based on the initial power level, the first response set is evaluated to determine whether a complete first package is present in the response set—that is, based on the collected tag responses, and the package content information of the tag responses, whether every article of a complete package is present in the response set as having responded to the RFID reader operating at the initial power level for the first period of time. Upon determining a complete package is present in the response set, the method 600 optionally includes a step of evaluating whether the complete package is of a type having an associated power level that matches the initial power level of the RFID reader in step 604.

Upon determining that the complete package is present, and the complete package is of a type having an associated power level matching the initial power level, the articles within the complete package are counted-in to the surgical procedure at step 610. It may occur that a complete package is found but that the articles are not of a type having an associated power level that matches the initial power level and, in that case, the articles are not counted-in to the surgical procedure.

Once the articles are counted-in after the initial operation of the RFID reader at an initial power level for the first period of time, the RFID reader may be reconfigured, at step 612, to operate at an incremented power level, different from the initial power level. The method may begin with the RFID reader at a low power level and increment to a higher power level, or alternatively may begin with the RFID at a higher power level and increment to a lower power level. At higher power level, it may be more likely that background tag responses from nearby stored articles may be received at the RFID reader. At lower power levels, fewer tag responses may be received from densely packed surgical articles as the tags in close proximity to each other cause interference or attenuation of the RFID reader's interrogator signal. Therefore, it is beneficial to cycle through the range of power levels within the capability of the RFID reader to ensure that the proper set of RFID tagged articles are counted into the surgical procedure.

The steps of operating the RFID reader at incrementing power levels, receiving response sets, and counting-in packages when they are determined complete and are of a type having an associated power level matching the power level of the cycled operation may be continued, along branch 613, until the desired RFID tagged article inventory is counted into the procedure. Once the desired inventory of surgical articles has been counted-in to the surgical procedure, the HCP may proceed with the surgical procedure as step 614. Upon completion of the surgical procedure, the surgical articles are removed from the patient at step 616. Following removal from the patient, the surgical articles are counted-out, for example, by again reading the surgical articles with the RFID reader, at step 618. In the count-out step 618 the RFID reader may operate at a default power level. In an alternative, the count-out step 618 may be similar to the count-out step 424, or step 518, both described above. In an alternative, counting-out the surgical article may include optically scanning a label provided on the surgical article, or manually entering information so as to designate the surgical article as counted-out. Consistent with the above description, the method 600 includes displaying the status of the article inventory, including, for example, providing an identification of counted-in and counted-out articles throughout the surgical procedure.

In one execution example, an inventory of sponges is provided, such as an inventory 112, at a step 402. An RFID reader, such as RFID reader 108, is provided and is toggled to operate in a count-in mode by providing an input at touchscreen 104 or the RFID reader 108. The RFID reader 108 is configured to initially operate at a default power level value of 15 dBm, which is stored in one of the system computer 101 or the RFID reader 108. The RFID reader 108 performs an interrogation cycle, such as at step 404, and receives the first response set of interrogation responses from a portion of the inventory presented to the RFID reader for counting-in. The system 100, either in the system computer 101 or the RFID reader 108, evaluates the first response set in order to identify at least 30% of sponges within a single package, such as at step 406. The RFID reader 108 determines two 18"×18" lap sponges are present in the first response set having the same unique package ID 126.

The RFID reader 108 reconfigures to operate at 14 dBm, such as at step 408, which is the power level parameter associated with the 18"×18" lap sponge type. The power level parameter is retrieved from a look-up table or database stored in the system computer 101 or the RFID reader 108. The RFID reader 108 performs an interrogation cycle at 14 dBm, such as at step 410. The RFID reader 108 receives the second response set, such as at step 412. The second response set includes response data from five 18"×18" lap sponges having the same Unique Pack ID 126, which represents a complete package. Optionally, the system may exclude any data in the second response set that does not correspond to the 18"×18" lap sponge type. The system 100 determines the complete package, such as at step 414, and counts-in the five 18"×18" lap sponges for use in the surgical operation, such as at step 416. The RFID reader 108 reconfigures to operate at the default power level and continues with the remainder of the inventory 112 until all necessary articles have been counted-in, such as at step 417. The RFID reader 108 follows the same sequence of detecting at least three out of ten 2"×2" gauge sponges in a package at the default power level, reconfiguring to operate at 25 dBm, and detecting ten out of ten sponges in a package at the 25 dBm power level to count-in a package of ten 2"×2" gauze sponges. Once the remainder of the inventory 112 has been counted-in, the surgery is performed with the counted-in articles, such as at step 420.

After the surgical operation has been completed, the counted-in articles are counted-out so that no articles are unintentionally retained in the patient following the procedure, such as at step 424. The RFID reader 108 is toggled to operate in the count-out mode by providing an input at touchscreen 104 or the RFID reader 108. The RFID reader 108 performs successive interrogation cycles at 14 dBm and 25 dBm in 300 ms intervals while looking for the counted-in 18"×18" lap sponges and the 2"×2" gauze sponges, respectively. The successive interrogations continue until all of one type of sponge is counted-out, after which successive interrogation cycles will occur only at the power level associated with the counted-in sponge type. Optionally, the system 100 may evaluate the RSSI associated with each sponge identified in the response set to ensure that a minimum response strength is present before the sponge is counted out.

Several descriptions have been discussed in the foregoing disclosure. However, the discussions herein are not intended to be exhaustive or limit any particular form. The terminology which has been used is intended to be in the nature of words of description rather than of limitation. Many modifications and variations are possible in light of the above teachings and the disclosure may be practiced otherwise than as specifically described.

What is claimed is:

1. A system for managing a supply of surgical sponges used during a surgical procedure to ensure proper removal of the surgical sponges following the surgical procedure, the supply comprising a first package containing a first surgical sponge of a first sponge type, wherein the first surgical sponge comprises a first RFID tag, the first RFID tag storing a first unique identifier associated with the first surgical sponge, first package content information, and a first assigned power level associated with the first sponge type, and wherein the first package content information corresponds to a complete content of the first package, the system comprising:

an RFID reader configurable to operate at one of a plurality of power levels in response to receiving a power level parameter in response to an RFID read operation; and a database configured to store data representing a status of the supply of surgical sponges identifying a counted-in quantity and a counted-out quantity, wherein the RFID reader is configured to:

operate at a first power level for a first limited period of time to read RFID tags of the supply of surgical sponges;

collect a first response set during the first limited period of time;

evaluate the first response set to determine whether the first response set matches the first package content information such that all surgical sponges within the first package are present in the first response set and to determine whether the first power level matches the first assigned power level associated with the first sponge type; and identify the first surgical sponge as counted-in in a database record for the surgical procedure responsive to determining that the first response set matches the first package content information and the first power level matches the first assigned power level associated with the first sponge type.

2. The system of claim 1, wherein the RFID reader is configured to:

responsive to identifying the first surgical sponge as counted-in:

reconfigure to operate at a second power level for a second limited period of time, the second power level different from the first power level;

read the first RFID tag; and identify the first surgical sponge as counted-out in the database record for the surgical procedure based on the reading of the first RFID tag.

3. The system of claim 1, comprising a display device configured to display the status of the supply of surgical sponges identifying the counted-in quantity and the counted-out quantity based on the database record.

4. The system of claim 1, wherein the supply of surgical sponges comprises a second package containing a second surgical sponge and a third surgical sponge, the second and third surgical sponges being of a second sponge type, wherein the second surgical sponge comprises a second RFID tag, the second RFID tag storing a second unique identifier associated with the second surgical sponge, second package content information, and a second assigned power level associated with the second sponge type, wherein the third surgical sponge comprises a third RFID tag, the third RFID tag storing a third unique identifier associated with the third surgical sponge, the second package content information, and the second assigned power level associated with the second sponge type, wherein the second package content information corresponds to a complete content of the second package, and wherein the RFID reader is configured to:

operate an RFID reader at a second power level for a second limited period of time;

collect a second response set during the second limited period of time;

evaluate the second response set to determine whether the second response set matches the second package content information such that all surgical sponges within the second package are present in the second response set and to determine whether the second power level matches the second assigned power level associated with the second sponge type; and identify the second and the third surgical sponges as counted-in in the database record for the surgical procedure responsive to determining that the second response set matches the second package content information and the second power level matches the second assigned power level associated with the second sponge type.

5. The system of claim 4, wherein the first package is larger than the second package, and the first assigned power level is greater than the second assigned power level.

6. The system of claim 4, wherein the first assigned power level is selected such that the first response set matches the first package content information when the first package is positioned within a preferred read range of the RFID reader defined by a non-zero first threshold distance and a second threshold distance greater than the first threshold distance, and such that the first response set does not match the first package content information when at least a portion the first package is separated from the RFID reader by a distance greater than the second threshold distance, and wherein the second assigned power level is selected such that the second response set matches the second package content information when the second package is within the preferred read range of the RFID reader, and such that the second response set does not match the second package content information when at least a portion of the second package is separated from the RFID reader by the distance greater than the second threshold distance.

7. The system of claim 6, wherein the first threshold distance is 12 inches and the second threshold distance is 36 inches.

8. The system of claim 1, wherein the RFID reader is configured to trigger an alert responsive to determining that the first power level matches the first assigned power level associated with the first sponge type and the first response set does not match the first package content information.

9. The system of claim 8, wherein the alert comprises any one of an alarm, a warning, a tactile response, or a combination thereof.

10. A method of managing an inventory of surgical sponges used during a surgical procedure to ensure proper removal of surgical sponges following the surgical procedure, the method comprising:

providing a supply of surgical sponges, the supply comprising a first package containing a first surgical sponge of a first sponge type, wherein the first surgical sponge comprises a first RFID tag, the first RFID tag storing a first unique identifier associated with the first surgical sponge, first package content information, and a first assigned power level associated with the first sponge type, wherein the first package content information corresponds to a complete content of the first package;

operating an RFID reader at a first power level for a first limited period of time to read RFID tags of the inventory of surgical sponges;

collecting a first response set during the first limited period of time;

determining that the first response set matches the first package content information such that all surgical sponges within the first package are present in the first response set and that the first power level matches the first assigned power level; and identifying the first surgical sponge as counted-in in a database record for the surgical procedure responsive to determining that the first response set matches the first package content information and the first power level matches the first assigned power level.

11. The method of claim 10, further comprising:

reconfiguring the RFID reader to operate at a second power level different from the first power level;

positioning the first surgical sponge in a body for the surgical procedure;

removing the first surgical sponge from the body;

operating the RFID reader and counting-out the first surgical sponge by reading the first RFID tag with the RFID reader; and displaying a status of the supply of surgical sponges providing a number of counted-in and counted-out surgical sponges for each type of surgical sponge.

12. The method of claim 10, wherein the supply of surgical sponges further comprises a second package containing a second surgical sponge and a third surgical sponge; the second and third surgical sponges being of a second sponge type, wherein the second surgical sponge comprises a second RFID tag, the second RFID tag storing a second unique identifier associated with the second surgical sponge, second package content information, and a second assigned power level associated with the second sponge type, wherein the third surgical sponge comprises a third RFID tag, the third RFID tag storing a third unique identifier associated with the third surgical sponge, the second package content information, and the second assigned power level associated with the second sponge type, and wherein the second package content information corresponds to a complete content of the second package; the method further comprising the steps of:

operating the RFID reader at a second power level for a second limited period of time;

collecting a second response set during the second limited period of time;

determining that the second response set matches the second package content information such that all surgical sponges within the second package are present in the second response set and that the second power level matches the second assigned power level; and identifying the second and the third surgical sponges as counted-in in the database record for the surgical procedure responsive to determining that the second response set matches the second package content information and that the second power level matches the second assigned power level.

13. The method of claim 12, comprising:

positioning the first package at a first distance from the RFID reader, the first distance being within a preferred read range for the RFID reader defined by a non-zero first threshold distance and a second threshold distance greater than the first threshold distance such that the first response set does not match the first package content information when at least a portion of the first package is separated from the RFID reader by a distance greater than the second threshold distance and the second response set does not match the second package content information when at least a portion of the second package is separated from the RFID reader by the distance greater than the second threshold distance; and positioning the second package at a second distance from the RFID reader, the second distance being within the preferred read range for the RFID reader, wherein the first package includes a first number of surgical sponges of the first sponge type and the second package includes a second number of surgical sponges of the second sponge type, the first number being greater than the second number, and wherein the first assigned power level is greater than the second assigned power level.

14. A system for managing a supply of surgical articles used during a surgical procedure to ensure proper removal of the surgical articles following the surgical procedure, the supply comprising a first package containing a first surgical article of a first article type, wherein the first surgical article comprises a first RFID tag, the first RFID tag storing a first unique identifier associated with the first surgical article, first package content information, and a first assigned power level associated with the first article type, and wherein the first package content information corresponds to a complete content of the first package, the system comprising:

an RFID reader configurable to operate at one of a plurality of power levels in response to receiving a power level parameter in response to an RFID read operation; and a database configured to store data representing a status of the supply of surgical articles identifying a counted-in quantity and a counted-out quantity, wherein the RFID reader is configured to:

operate at a first power level for a first limited period of time to read RFID tags of the supply of surgical articles;

collect a first response set during the first limited period of time;

evaluate the first response set to determine whether the first response set matches the first package content information such that all surgical articles within the first package are present in the first response set and to determine whether the first power level matches the first assigned power level associated with the first article type; and identify the first surgical article as counted-in in a database record for the surgical procedure responsive to determining that the first response set matches the first package content information and that the first power level matches the first assigned power level associated with the first article type.

15. The system of claim 14, wherein the RFID reader is configured to:

responsive to identifying the first surgical article as counted-in:

reconfigure to operate at a second power level for a second limited period of time, the second power level different from the first power level;

read the first RFID tag; and identify the first surgical article as counted-out in the database record for the surgical procedure based on the reading of the first RFID tag.

16. The system of claim 14, further comprising a display device configured to display the status of the supply of surgical articles identifying the counted-in quantity and the counted-out quantity based on the database record.

17. The system of claim 14, wherein the supply of surgical articles comprises a second package containing a second surgical article and a third surgical article, the second and third surgical articles being of a second article type, wherein the second surgical article comprises a second RFID tag, the second RFID tag storing a second unique identifier associated with the second surgical article, second package content information, and a second assigned power level associated with the second article type, wherein the third surgical article comprises a third RFID tag, the third RFID tag storing a third unique identifier associated with the third surgical article, the second package content information, and the second assigned power level associated with the second article type, wherein the second package content information corresponds to a complete content of the second package, and wherein the RFID reader is configured to:

operate an RFID reader at a second power level for a second limited period of time;

collect a second response set during the second limited period of time;

evaluate the second response set to determine whether the second response set matches the second package content information such that all surgical articles within the second package are present in the second response set and to determine whether the second power level matches the second assigned power level associated with the second article type; and identify the second and the third surgical articles as counted-in in the database record for the surgical procedure responsive to determining that the second response set matches the second package content information and the second power level matches the second assigned power level associated with the second article type.

18. The system of claim 17, wherein the first package is larger than the second package, and the first assigned power level is greater than the second assigned power level.

19. The system of claim 17, wherein the first assigned power level is selected such that the first response set matches the first package content information when the first package is positioned within a preferred read range of the RFID reader defined by a non-zero first threshold distance and a second threshold distance greater than the first threshold distance, and such that the first response set does not match the first package content information when at least a portion the first package is separated from the RFID reader by a distance greater than the second threshold distance, and wherein the second assigned power level is selected such that the second response set matches the second package content information when the second package is within the preferred read range of the RFID reader, and such that the second response set does not match the second package content information when at least a portion of the second package is separated from the RFID reader by the distance greater than the second threshold distance.

20. The system of claim 14, wherein the RFID reader is configured to trigger an alert responsive to determining that the first power level matches the first assigned power level associated with the first article type and the first response set does not match the first package content information.

* * * * *